US006524806B1

(12) United States Patent
Snodgrass et al.

(10) Patent No.: US 6,524,806 B1
(45) Date of Patent: Feb. 25, 2003

(54) METHODS OF SCREENING FOR LIGANDS OF HUMAN HEMETOPOIETIN RECEPTOR HU-B1.219

(75) Inventors: H. Ralph Snodgrass, Powell, OH (US); Joseph Cioffi, Athens, OH (US); Thomas Joel Zupancic, Worthington, OH (US); Alan Wayne Shafer, Albany, OH (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 09/357,914

(22) Filed: Jul. 19, 1999

Related U.S. Application Data

(63) Continuation of application No. 08/693,696, filed on Aug. 5, 1996, now Pat. No. 6,005,080, which is a division of application No. 08/355,888, filed on Dec. 14, 1994, now Pat. No. 5,763,211, which is a continuation-in-part of application No. 08/306,231, filed on Sep. 14, 1994, now Pat. No. 5,643,748.

(51) Int. Cl.[7] ............................................. G01N 33/566

(52) U.S. Cl. ...................... 435/7.21; 435/7.24; 435/7.9; 435/29; 436/501

(58) Field of Search .............................. 435/6, 7.1, 7.2, 435/7.21, 29, 40.5, 325, 320.1; 436/501, 503, 504; 530/350; 536/23.5, 23.4

(56) References Cited

U.S. PATENT DOCUMENTS 5,972,621 A * 10/1999 Tartaglia et al. ............. 435/7.1

FOREIGN PATENT DOCUMENTS

| EP | 0 409 607 | 7/1989 |
| EP | 0 521 156 | 1/1993 |
| WO | WO 88/02757 | 4/1988 |
| WO | WO 93/10151 | 5/1993 |
| WO | WO 9607737 | 3/1996 |

OTHER PUBLICATIONS

Bahary et al., 1990, "Molecular Mapping of the Mouse db Mutation," *Proc. Natl. Acad. Sci. U.S.A.* 87:8642–8646.

Barr et al., 1999, "Subcellular localization and internalization of the four human leptin receptor isoforms," *J. Biol. Chem.* 274(30):21416–21424.

Baumann et al., 1996, "The full–length leptin receptor has signaling capabilities of interleukin 6–type cytokine receptors," *Proc. Natl. Acad. Sci. U.S.A.* 93(16):8374–8378.

Bazan, 1990, "Structural Design And Molecular Evolution Of A Cytokine Receptor Superfamily," *Proc. Natl. Acad. Sci. U.S.A.* 87:6934–6938.

Beckmann et al., 1994, "Molecular Characterization of a Family of Ligands for eph–Related Tyrosine Kinase Receptors," *EMBO Journal* 13(16):3757–3762.

Bennett et al., 1996, "A role for leptin and its cognate receptor in hematopoiesis," *Curr. Biol.* 6(9):1170–1180.

Cheng et al., 1994, "Role of leukemia inhibitory factor and its receptor in mouse primordial germ cell growth," *Development* 120(11):3145–3153.

(List continued on next page.)

*Primary Examiner*—David Saunders
(74) *Attorney, Agent, or Firm*—Pennie & Edmonds LLP

(57) ABSTRACT

The present invention relates to a novel member of the hematopoietin receptor family, herein referred to as Hu-B1.219. In particular, the invention relates to nucleotide sequences and expression vectors encoding Hu-B1.219 gene product. Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

77 Claims, 11 Drawing Sheets

OTHER PUBLICATIONS

Figure 1:
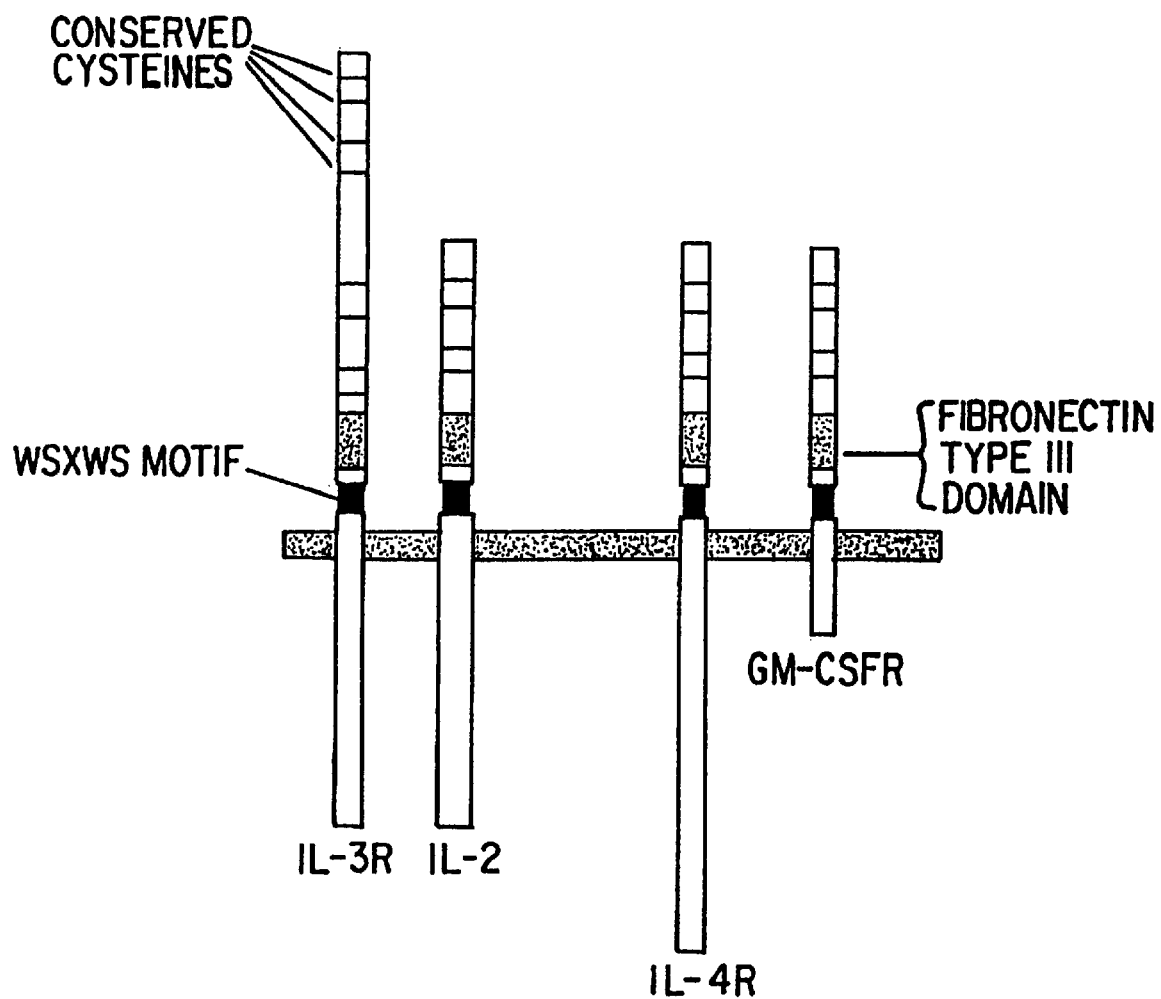

Cioffi et al., 1996, "Novel B219/OB Receptor Isoforms: Possible Roles of Leptin in Hematopoiesis and Reproduction," *Nature Medicine* 2(5):585–589.

Cosman et al., 1990, "A New Cytokine Receptor Superfamily," *Trends Biochem. Sci.* 15(7):265–270.

Crouse et al., 1998, "Altered cell surface expression and signaling of leptin receptors containing fatty mutation," *J. Biol. Chem.* 273(29):18365–18373.

Dusanter–Fourt et al., 1994, "Transduction du Signal Par Les Recepteurs De Cytokines," *Medicine Sciences* 10:825–835.

Fukunaga et al., 1990, "Expression Cloning Of A Receptor For Murine Granulocyte Colony–Stimulating Factor," *Cell* 61:341–350.

Gearing et al., 1987, "Molecular Cloning And Expression Of cDNA Encoding A Murine Myeloid Leukaemia Inhibitory Factor (LIF)," *EMBO J.* 6:3995–4002.

Gearing et al., 1989, "Expression Cloning Of A Receptor For Human Granulocyte–Macrophage Colony–Stimulating Factor," *EMBO J.* 8:3667–7676.

Gorman et al., 1990, "Cloning and Expression Of A Gene Encoding An Interleukin 3 Receptor–Like Protein: Identification Of Another Member Of The Cytokine Receptor Gene Family," *Proc. Natl. Acad. Sci. U.S.A.* 87:5459–5463.

Harada et al., 1990, "Expression Cloning Of A cDNA Encoding The Murine Interleukin 4 Receptor Based On Ligand Binding," *Proc. Natl. Acad. Sci. U.S.A.* 87:857–861.

Harlow and Lane. *Antibodies: A Laboratory Manual.* Cold Spring Harbor Laboratory, Cold Spring Harbor, NY. pp. 23–26, 72–77, 92–97, 128–135, 141–157, 613–633. 1988.

Hayashida et al.,1990, "Molecular Cloning Of A Second Subunit Of The Receptor For Human Granulocyte–Macrophage Colony–Stimulating Factor (GM–CSF): Reconstitution Of A High Affinity GM–CSF Receptor," *Proc. Natl. Acad. Sci. U.S.A.* 87:9655–9659.

Hibi et al., 1990, "Molecular Cloning And Expression Of An IL–6 Signal Transducer, gp130," *Cell* 63:1149–1157.

Jacobs et al., 1983, "Isolation and Characterization of genomic and cDNA clones of human erythropoietin," *Nature* 313(6005):806–810.

Lai et al., 1991, "The effects of blockade of interleukin 2 receptors and interleukin 4 receptors on cytokine production," *APMIS* 99(5):434–442.

Larsen et al., 1990, "Expression Cloning Of A Human Granulocyte Colony–Stimulating Factor Receptor: A Structural Mosaic Of Hematopoietin Receptor, Immunoglobulin, And Fibronectin Domains," *J. Exp. Med.* 172:1559–1570.

Miyajima et al., 1992, "Cytokine Receptors And Signal Transduction," *Annu. Rev. Immunol.* 19:295–331.

Miyajima et al., 1993, "Receptors For Granulocyte–Macrophage Colony–Stimulating Factor, Interleukin–3, and Interleukin–5," *Blood* 82(7):1960–1974.

Mosely et al., 1989, "The Murine Interleukin–4 Receptor: Molecular Cloning And Characterization Of Secreted And Membrane Bound Forms," *Cell* 59:335–348.

Murakami et al., 1997, "A short form of leptin reeptor performs signal transduction," *Biochem. Biophys. Res. Commun.* 231(1):26–29.

Ono et al., 1987, "A Novel Human Nonviral Retroposon Derived From An Endogenous Retrovirus," *Nucleic Acid. Res.* 15:8725–8737.

Park et al., 1992, "Cloning Of The Low–Affinity Murine Granulocyte–Macrophage Colony–Stimulating Factor Receptor And Reconstitution Of A High–Affinity Receptor Complex," *Proc. Natl. Acad. Sci. U.S.A.* 89:4295–4299.

Saito et al., 1992, "Molecular Cloning Of A Murine IL–6 Receptor–Associated Signal Transducer, gp130, And Its Regulated Expression In Vivo," *J. Immunol.* 148:4066–4071.

Seed and Aruffo, 1987, "Molecular cloning of the CD2 antigen, the T–cell erythrocyte receptor, by a rapid immunoselection procedure," *Proc. Natl. Acad. Sci. U.S.A.* 84(10):3365–3369.

Singer, 1982, "SINEs AND LINEs: Highly Repeated Short And Long Interspersed Sequences In Mammalian Genomes," *Cell* 28:433–434.

Streamson et al., 1996, "Phenotypes of Mouse diabetes and Rat fatty Due to Mutations in the OB (Leptin) Receptor," *Science* 271:994–996.

Taga et al., 1992, "Functional inhibition of hematopoietic and neurotrophic cytokines by blocking the interleukin 6 signal transducer gp130," *Proc. Natl. Acad. Sci. U.S.A.* 89(22):10998–10998–11001.

Tartaglia et al., 1995, "Identification and Expression Cloning of a Leptin Receptor, OB–R," *Cell* 83:1263–1271.

Truett et al., 1991, "Rat Obesity Gene fatty (fa) Mapps to Chromosome 5: Evidence for Homology with the Mouse Gene diabetes (db)," *Proc. Natl. Acad. Sci. U.S.A.* 88:7806–7809.

Wang et al., 1997, "Leptin receptor action in hepatic cells," J. Biol. Chem. 272(26):16216–16223.

White et al., 1997, "Leptin receptor (OB–R) signaling. Cytoplasmic domain mutational analysis and evidence for receptor homo–oligomerization," *J. Biol. Chem.* 272(7):4065–4071.

Wong et al., 1985, "Human FM–CSF: molecular cloning of the complementary DNA and purification of the natural and recombinant proteins," *Science* 228(4701):810–815.

Yamasaki et al., 1988, "Cloning And Expression Of The Human Interleukin–6 (BSF–2/IFNβ 2) Receptor," *Science* 241:825–828.

Zhang et al., 1994, "Ciliary neurotrophic factor, interleukin 11, leukemia inhibitory factor, and oncostatin M are growth factors for human myeloma cell lines using the interleukin 6 signal transducer gp130," *J. Exp. Med.* 179(4):1337–1342.

* cited by examiner

```
              9              18              27              36              45              54
GCG CGC GCG ACG CAG GTG CCC GAG CCC CGG CCC GCG CCC ATC TCT GCC TTC GGT
--- --- --- --- --- --- --- --- --- --- --- --- --- --- --- --- --- ---
 A   R   A   T   Q   V   P   E   P   R   P   A   P   I   S   A   F   G 63              72              81              90              99             108
CGA GTT GGA CCC CCG GAT CAA GGT GTA CTT CTC TGA AGT AAG ATG ATT TGT CAA
--- --- --- --- --- --- --- --- --- --- --- --- --- --- --- --- --- ---
 R   V   G   P   P   D   Q   G   V   L   L   *   S   K   M   I   C   Q 117             126             135             144             153             162
AAA TTC TGT GTG GTT TTG TTA CAT TGG GAA TTT ATT TAT GTG ATA ACT GCG TTT
--- --- --- --- --- --- --- --- --- --- --- --- --- --- --- --- --- ---
 K   F   C   V   V   L   L   H   W   E   F   I   Y   V   I   T   A   F 171             180             189             198             207             216
AAC TTG TCA TAT CCA ATT ACT CCT TGG AGA TTT AAG TTG TCT TGC ATG CCA CCA
--- --- --- --- --- --- --- --- --- --- --- --- --- --- --- --- --- ---
 N   L   S   Y   P   I   T   P   W   R   F   K   L   S   C   M   P   P 225             234             243             252             261             270
AAT TCA ACC TAT GAC TAC TTC CTT TTG CCT GCT GGA CTC TCA AAG AAT ACT TCA
--- --- --- --- --- --- --- --- --- --- --- --- --- --- --- --- --- ---
 N   S   T   Y   D   Y   F   L   L   P   A   G   L   S   K   N   T   S 279             288             297             306             315             324
AAT TCG AAT GGA CAT TAT GAG ACA GCT GTT GAA CCT AAG TTT AAT TCA AGT GGT
--- --- --- --- --- --- --- --- --- --- --- --- --- --- --- --- --- ---
 N   S   N   G   H   Y   E   T   A   V   E   P   K   F   N   S   S   G 333             342             351             360             369             378
ACT CAC TTT TCT AAC TTA TCC AAA GCA ACT TTC CAC TGT TGC TTT CGG AGT GAG
--- --- --- --- --- --- --- --- --- --- --- --- --- --- --- --- --- ---
 T   H   F   S   N   L   S   K   A   T   F   H   C   C   F   R   S   E 387             396             405             414             423             432
CAA GAT AGA AAC TGC TCC TTA TGT GCA GAC AAC ATT GAA GGA AGG ACA TTT GTT
--- --- --- --- --- --- --- --- --- --- --- --- --- --- --- --- --- ---
 Q   D   R   N   C   S   L   C   A   D   N   I   E   G   R   T   F   V
```

FIG.2A

```
     441         450         459         468         477         486
TCA ACA GTA AAT TCT TTA GTT TTT CAA CAA ATA GAT GCA AAC TGG AAC ATA CAG
--- --- --- --- --- --- --- --- --- --- --- --- --- --- --- --- --- ---
 S   T   V   N   S   L   V   F   Q   Q   I   D   A   N   W   N   I   Q 495         504         513         522         531         540
TGC TGG CTA AAA GGA GAC TTA AAA TTA TTC ATC TGT TAT GTG GAG TCA TTA TTT
--- --- --- --- --- --- --- --- --- --- --- --- --- --- --- --- --- ---
 C   W   L   K   G   D   L   K   L   F   I   C   Y   V   E   S   L   F 549         558         567         576         585         594
AAG AAT CTA TTC AGG AAT TAT AAC TAT AAG GTC CAT CTT TTA TAT GTT CTG CCT
--- --- --- --- --- --- --- --- --- --- --- --- --- --- --- --- --- ---
 K   N   L   F   R   N   Y   N   Y   K   V   H   L   L   Y   V   L   P 603         612         621         630         639         648
GAA GTG TTA GAA GAT TCA CCT CTG GTT CCC CAA AAA GGC AGT TTT CAG ATG GTT
--- --- --- --- --- --- --- --- --- --- --- --- --- --- --- --- --- ---
 E   V   L   E   D   S   P   L   V   P   Q   K   G   S   F   Q   M   V 657         666         675         684         693         702
CAC TGC AAT TGC AGT GTT CAT GAA TGT TGT GAA TGT CTT GTG CCT GTG CCA ACA
--- --- --- --- --- --- --- --- --- --- --- --- --- --- --- --- --- ---
 H   C   N   C   S   V   H   E   C   C   E   C   L   V   P   V   P   T 711         720         729         738         747         756
GCC AAA CTC AAC GAC ACT CTC CTT ATG TGT TTG AAA ATC ACA TCT GGT GGA GTA
--- --- --- --- --- --- --- --- --- --- --- --- --- --- --- --- --- ---
 A   K   L   N   D   T   L   L   M   C   L   K   I   T   S   G   G   V 765         774         783         792         801         810
ATT TTC CGG TCA CCT CTA ATG TCA GTT CAG CCC ATA AAT ATG GTG AAG CCT GAT
--- --- --- --- --- --- --- --- --- --- --- --- --- --- --- --- --- ---
 I   F   R   S   P   L   M   S   V   Q   P   I   N   M   V   K   P   D 819         828         837         846         855         864
CCA CCA TTA GGT TTG CAT ATG GAA ATC ACA GAT GAT GGT AAT TTA AAG ATT TCT
--- --- --- --- --- --- --- --- --- --- --- --- --- --- --- --- --- ---
 P   P   L   G   L   H   M   E   I   T   D   D   G   N   L   K   I   S
```

FIG.2B

```
       873           882           891           900           909           918
TGG TCC AGC CCA CCA TTG GTA CCA TTT CCA CTT CAA TAT CAA GTG AAA TAT TCA
--- --- --- --- --- --- --- --- --- --- --- --- --- --- --- --- --- ---
 W   S   S   P   P   L   V   P   F   P   L   Q   Y   Q   V   K   Y   S 927           936           945           954           963           972
GAG AAT TCT ACA ACA GTT ATC AGA GAA GCT GAC AAG ATT GTC TCA GCT ACA TCC
--- --- --- --- --- --- --- --- --- --- --- --- --- --- --- --- --- ---
 E   N   S   T   T   V   I   R   E   A   D   K   I   V   S   A   T   S 981           990           999          1008          1017          1026
CTG CTA GTA GAC AGT ATA CTT CCT GGG TCT TCG TAT GAG GTT CAG GTG AGG GGC
--- --- --- --- --- --- --- --- --- --- --- --- --- --- --- --- --- ---
 L   L   V   D   S   I   L   P   G   S   S   Y   E   V   Q   V   R   G 1035          1044          1053          1062          1071          1080
AAG AGA CTG GAT GGC CCA GGA ATC TGG AGT GAC TGG AGT ACT CCT CGT GTC TTT
--- --- --- --- --- --- --- --- --- --- --- --- --- --- --- --- --- ---
 K   R   L   D   G   P   G   I   W   S   D   W   S   T   P   R   V   F 1089          1098          1107          1116          1125          1134
ACC ACA CAA GAT GTC ATA TAC TTT CCA CCT AAA ATT CTG ACA AGT GTT GGG TCT
--- --- --- --- --- --- --- --- --- --- --- --- --- --- --- --- --- ---
 T   T   Q   D   V   I   Y   F   P   P   K   I   L   T   S   V   G   S 1143          1152          1161          1170          1179          1188
AAT GTT TCT TTT CAC TGC ATC TAT AAG AAG GAA AAC AAG ATT GTT CCC TCA AAA
--- --- --- --- --- --- --- --- --- --- --- --- --- --- --- --- --- ---
 N   V   S   F   H   C   I   Y   K   K   E   N   K   I   V   P   S   K 1197          1206          1215          1224          1233          1242
GAG ATT GTT TGG TGG ATG AAT TTA GCT GAG AAA ATT CCT CAA AGC CAG TAT GAT
--- --- --- --- --- --- --- --- --- --- --- --- --- --- --- --- --- ---
 E   I   V   W   W   M   N   L   A   E   K   I   P   Q   S   Q   Y   D 1251          1260          1269          1278          1287          1296
GTT GTG AGT GAT CAT GTT AGC AAA GTT ACT TTT TTC AAT CTG AAT GAA ACC AAA
--- --- --- --- --- --- --- --- --- --- --- --- --- --- --- --- --- ---
 V   V   S   D   H   V   S   K   V   T   F   F   N   L   N   E   T   K
```

FIG.2C

```
      1305          1314          1323          1332          1341          1350
CCT CGA GGA AAG TTT ACC TAT GAT GCA GTG TAC TGC TGC AAT GAA CAT GAA TGC
--- --- --- --- --- --- --- --- --- --- --- --- --- --- --- --- --- ---
 P   R   G   K   F   T   Y   D   A   V   Y   C   C   N   E   H   E   C 1359          1368          1377          1386          1395          1404
CAT CAT CGC TAT GCT GAA TTA TAT GTG ATT GAT GTC AAT ATC AAT ATC TCA TGT
--- --- --- --- --- --- --- --- --- --- --- --- --- --- --- --- --- ---
 H   H   R   Y   A   E   L   Y   V   I   D   V   N   I   N   I   S   C 1413          1422          1431          1440          1449          1458
GAA ACT GAT GGG TAC TTA ACT AAA ATG ACT TGC AGA TGG TCA ACC AGT ACA ATC
--- --- --- --- --- --- --- --- --- --- --- --- --- --- --- --- --- ---
 E   T   D   G   Y   L   T   K   M   T   C   R   W   S   T   S   T   I 1467          1476          1485          1494          1503          1512
CAG TCA CTT GCG GAA AGC ACT TTG CAA TTG AGG TAT CAT AGG AGC AGC CTT TAC
--- --- --- --- --- --- --- --- --- --- --- --- --- --- --- --- --- ---
 Q   S   L   A   E   S   T   L   Q   L   R   Y   H   R   S   S   L   Y 1521          1530          1539          1548          1557          1566
TGT TCT GAT ATT CCA TCT ATT CAT CCC ATA TCT GAG CCC AAA GAT TGC TAT TTG
--- --- --- --- --- --- --- --- --- --- --- --- --- --- --- --- --- ---
 C   S   D   I   P   S   I   H   P   I   S   E   P   K   D   C   Y   L 1575          1584          1593          1602          1611          1620
CAG AGT GAT GGT TTT TAT GAA TGC ATT TTC CAG CCA ATC TTC CTA TTA TCT GGC
--- --- --- --- --- --- --- --- --- --- --- --- --- --- --- --- --- ---
 Q   S   D   G   F   Y   E   C   I   F   Q   P   I   F   L   L   S   G 1629          1638          1647          1656          1665          1674
TAC ACA ATG TGG ATT AGG ATC AAT CAC TCT CTA GGT TCA CTT GAC TCT CCA CCA
--- --- --- --- --- --- --- --- --- --- --- --- --- --- --- --- --- ---
 Y   T   M   W   I   R   I   N   H   S   L   G   S   L   D   S   P   P 1683          1692          1701          1710          1719          1728
ACA TGT GTC CTT CCT GAT TCT GTG GTG AAG CCA CTG CCT CCA TCC AGT GTG AAA
--- --- --- --- --- --- --- --- --- --- --- --- --- --- --- --- --- ---
 T   C   V   L   P   D   S   V   V   K   P   L   P   P   S   S   V   K
```

FIG.2D

```
          1737           1746          1755           1764          1773           1782
GCA GAA ATT ACT ATA AAC ATT GGA TTA TTG AAA ATA TCT TGG GAA AAG CCA GTC
--- --- --- --- --- --- --- --- --- --- --- --- --- --- --- --- --- ---
 A   E   I   T   I   N   I   G   L   L   K   I   S   W   E   K   P   V 1791           1800          1809           1818          1827           1836
TTT CCA GAG AAT AAC CTT CAA TTC CAG ATT CGC TAT GGT TTA AGT GGA AAA GAA
--- --- --- --- --- --- --- --- --- --- --- --- --- --- --- --- --- ---
 F   P   E   N   N   L   Q   F   Q   I   R   Y   G   L   S   G   K   E 1845           1854          1863           1872          1881           1890
GTA CAA TGG AAG ATG TAT GAG GTT TAT GAT GCA AAA TCA AAA TCT GTC AGT CTC
--- --- --- --- --- --- --- --- --- --- --- --- --- --- --- --- --- ---
 V   Q   W   K   M   Y   E   V   Y   D   A   K   S   K   S   V   S   L 1899           1908          1917           1926          1935           1944
CCA GTT CCA GAC TTG TGT GCA GTC TAT GCT GTT CAG GTG CGC TGT AAG AGG CTA
--- --- --- --- --- --- --- --- --- --- --- --- --- --- --- --- --- ---
 P   V   P   D   L   C   A   V   Y   A   V   Q   V   R   C   K   R   L 1953           1962          1971           1980          1989           1998
GAT GGA CTG GGA TAT TGG AGT AAT TGG AGC AAT CCA GCC TAC ACA GTT GTC ATG
--- --- --- --- --- --- --- --- --- --- --- --- --- --- --- --- --- ---
 D   G   L   G   Y   W   S   N   W   S   N   P   A   Y   T   V   V   M 2007           2016          2025           2034          2043           2052
GAT ATA AAA GTT CCT ATG AGA GGA CCT GAA TTT TGG AGA ATA ATT AAT GGA GAT
--- --- --- --- --- --- --- --- --- --- --- --- --- --- --- --- --- ---
 D   I   K   V   P   M   R   G   P   E   F   W   R   I   I   N   G   D 2061           2070          2079           2088          2097           2106
ACT ATG AAA AAG GAG AAA AAT GTC ACT TTA CTT TGG AAG CCC CTG ATG AAA AAT
--- --- --- --- --- --- --- --- --- --- --- --- --- --- --- --- --- ---
 T   M   K   K   E   K   N   V   T   L   L   W   K   P   L   M   K   N 2115           2124          2133           2142          2151           2160
GAC TCA TTG TGC AGT GTT CAG AGA TAT GTG ATA AAC CAT CAT ACT TCC TGC AAT
--- --- --- --- --- --- --- --- --- --- --- --- --- --- --- --- --- ---
 D   S   L   C   S   V   Q   R   Y   V   I   N   H   H   T   S   C   N
```

FIG.2E

```
      2169        2178        2187        2196        2205        2214
GGA ACA TGG TCA GAA GAT GTG GGA AAT CAC ACG AAA TTC ACT TTC CTG TGG ACA
--- --- --- --- --- --- --- --- --- --- --- --- --- --- --- --- --- ---
 G   T   W   S   E   D   V   G   N   H   T   K   F   T   F   L   W   T 2223        2232        2241        2250        2259        2268
GAG CAA GCA CAT ACT GTT ACG GTT CTG GCC ATC AAT TCA ATT GGT GCT TCT GTT
--- --- --- --- --- --- --- --- --- --- --- --- --- --- --- --- --- ---
 E   Q   A   H   T   V   T   V   L   A   I   N   S   I   G   A   S   V 2277        2286        2295        2304        2313        2322
GCA AAT TTT AAT TTA ACC TTT TCA TGG CCT ATG AGC AAA GTA AAT ATC GTG CAG
--- --- --- --- --- --- --- --- --- --- --- --- --- --- --- --- --- ---
 A   N   F   N   L   T   F   S   W   P   M   S   K   V   N   I   V   Q 2331        2340        2349        2358        2367        2376
TCA CTC AGT GCT TAT CCT TTA AAC AGC AGT TGT GTG ATT GTT TCC TGG ATA CTA
--- --- --- --- --- --- --- --- --- --- --- --- --- --- --- --- --- ---
 S   L   S   A   Y   P   L   N   S   S   C   V   I   V   S   W   I   L 2385        2394        2403        2412        2421        2430
TCA CCC AGT GAT TAC AAG CTA ATG TAT TTT ATT ATT GAG TGG AAA AAT CTT AAT
--- --- --- --- --- --- --- --- --- --- --- --- --- --- --- --- --- ---
 S   P   S   D   Y   K   L   M   Y   F   I   I   E   W   K   N   L   N 2439        2448        2457        2466        2475        2484
GAA GAT GGT GAA ATA AAA TGG CTT AGA ATC TCT TCA TCT GTT AAG AAG TAT TAT
--- --- --- --- --- --- --- --- --- --- --- --- --- --- --- --- --- ---
 E   D   G   E   I   K   W   L   R   I   S   S   S   V   K   K   Y   Y 2493        2502        2511        2520        2529        2538
ATC CAT GAT CAT TTT ATC CCC ATT GAG AAG TAC CAG TTC AGT CTT TAC CCA ATA
--- --- --- --- --- --- --- --- --- --- --- --- --- --- --- --- --- ---
 I   H   D   H   F   I   P   I   E   K   Y   Q   F   S   L   Y   P   I 2547        2556        2565        2574        2583        2592
TTT ATG GAA GGA GTG GGA AAA CCA AAG ATA ATT AAT AGT TTC ACT CAA GAT GAT
--- --- --- --- --- --- --- --- --- --- --- --- --- --- --- --- --- ---
 F   M   E   G   V   G   K   P   K   I   I   N   S   F   T   Q   D   D
```

FIG.2F

```
        2601          2610          2619          2628          2637          2646
ATT GAA AAA CAC CAG AGT GAT GCA GGT TTA TAT GTA ATT GTG CCA GTA ATT ATT
--- --- --- --- --- --- --- --- --- --- --- --- --- --- --- --- --- ---
 I   E   K   H   Q   S   D   A   G   L   Y   V   I   V   P   V   I   I 2655          2664          2673          2682          2691          2700
TCC TCT TCC ATC TTA TTG CTT GGA ACA TTA TTA ATA TCA CAC CAA AGA ATG AAA
--- --- --- --- --- --- --- --- --- --- --- --- --- --- --- --- --- ---
 S   S   S   I   L   L   L   G   T   L   L   I   S   H   Q   R   M   K 2709          2718          2727          2736          2745          2754
AAG CTA TTT TGG GAA GAT GTT CCG AAC CCC AAG AAT TGT TCC TGG GCA CAA GGA
--- --- --- --- --- --- --- --- --- --- --- --- --- --- --- --- --- ---
 K   L   F   W   E   D   V   P   N   P   K   N   C   S   W   A   Q   G 2763          2772          2781          2790          2799          2808
CTT AAT TTT CAG AAG ATG CTT GAA GGC AGC ATG TTC GTT AAG AGT CAT CAC CAC
--- --- --- --- --- --- --- --- --- --- --- --- --- --- --- --- --- ---
 L   N   F   Q   K   M   L   E   G   S   M   F   V   K   S   H   H   H 2817          2826          2835          2844          2853          2862
TCC CTA ATC TCA AGT ACC CAG GGA CAC AAA CAC TGC GGA AGG CCA CAG GGT CCT
--- --- --- --- --- --- --- --- --- --- --- --- --- --- --- --- --- ---
 S   L   I   S   S   T   Q   G   H   K   H   C   G   R   P   Q   G   P 2871          2880          2889          2898          2907          2916
CTG CAT AGG AAA ACC AGA GAC CTT TGT TCA CTT GTT TAT CTG CTG ACC CTC CCT
--- --- --- --- --- --- --- --- --- --- --- --- --- --- --- --- --- ---
 L   H   R   K   T   R   D   L   C   S   L   V   Y   L   L   T   L   P 2925          2934          2943          2952          2961          2970
CCA CTA TTG TCC TAT GAC CCT GCC AAA TCC CCC TCT GTG AGA AAC ACC CAA GAA
--- --- --- --- --- --- --- --- --- --- --- --- --- --- --- --- --- ---
 P   L   L   S   Y   D   P   A   K   S   P   S   V   R   N   T   Q   E 2979          2988
TGA TCA ATA AAA AAA AAA AAA 3'
--- --- --- --- --- --- ---
 *   S   I   K   K   K   K
```

FIG.2G

```
                   2760       2770       2780       2790       2800
HuB1.219 Form 1 2751 AGGACTTAAT TTTCAGAAGA TGCTTGAAGG CAGCATGTTC GTTAAGAGTC 2800
HuB1.219      2 2751 AGGACTTAAT TTTCAGAAGA AAATGCCTGG CACAAAGGAA CTACTGGGTG 2800
HuB1.219      3 2751 AGGACTTAAT TTTCAGAAGA GAACGGACAT TCTTTGAAGT CTAATCATGA 2800

2810       2820       2830       2840       2850
HuB1.219 Form 1 2801 ATCACCACTC CCTAATCTCA AGTACCCAGG GACACAAACA CTGCGGAAGG 2850
HuB1.219      2 2801 GAGGTTGGTT GACTTAGGAA ATGCTTGTGA AGCTACGTCC TACCTCGTGC 2850
HuB1.219      3 2801 TCACTACAGA TGAACCCAAT GTGCCAACTT CCCAACAGTC TATAGAGTAT 2850

2860       2870       2880       2890       2900
HuB1.219 Form 1 2851 CCACAGGGTC CTCTGCATAG GAAAACCAGA GACCTTTGTT CACTTGTTTA 2900
HuB1.219      2 2851 GCACCTGCTC TCCCTGAGGT GTGCACAATG .......... .......... 2900
HuB1.219      3 2851 TAGAAGATTT TTACATTCTG AAGAAGG... .......... ..........
   2900
                   2910       2920       2930       2940       2950
HuB1.219 Form 1 2901 TCTGCTGACC CTCCCTCCAC TATTGTCCTA TGACCCTGCC AAATCCCCCT 2950
HuB1.219      2 2901 .......... .......... .......... .......... .......... 2950
HuB1.219      3 2901 .......... .......... .......... .......... .......... 2950

2960       2970       2980       2990       3000
HuB1.219 Form 1 2951 CTGTGAGAAA CACCCAAGAA TGATCAATAA AAAAAAAAAA A......... 3000
HuB1.219      2 2951 .......... .......... .......... .......... .......... 3000
HuB1.219      3 2951 .......... .......... .......... .......... .......... 3000
```

FIG.3A

```
                    10         20         30         40         50
HuB1.219 Form 1  1 GLNFQKMLEG SMFVKSHHHS LISSTQGHKH CGRPQGPLHR KTRDLCSLVY  50
HuB1.219      2  1 GLNFQKKMPG TKELLGGGWL T*EMLVKLRP TSCAPALPEV CTM.......  50
HuB1.219      3  1 GLNFQKRTDI L*SLIMITTD EPNVPTSQQS IEY*KIFTF* RR........  50

60         70         80         90        100
HuB1.219 Form 1 51 LLTLPPLLSY DPAKSPSVRN TQE*SIKKKK .......... .......... 100
HuB1.219      2 51 .......... .......... .......... .......... .......... 100
HuB1.219      3 51 .......... .......... .......... .......... .......... 100
```

FIG.3B

SPACING OF CONSERVED AMINO ACIDS IN THE EXTRACELLULAR DOMAINS OF KNOWN CYTOKINE RECEPTOR GENES

```
..C...C.............C....C............A/PP.L/V.....W.....Y..........L...Y..R...G.WSXWS..
 (10-11)    (28-35)  (9-16)    (36-48)    (2-3) (13-18)(12-20) (26-33) (5-6)(5)(6-11)(2)
```

CONSERVED AMINO ACIDS IN THE 5' EXTRACELLULAR DOMAINS OF CLONE Hu-B1.219

```
..C...C..........C....C..............PP.L.......W.....Y..........L...Y..R...G.WSDWS..
  (11)     (44)     (10)         (43)      (3)  (14)   (12)     (30)    (5) (5)(8)(2)
```

CONSERVED AMINO ACIDS IN THE 3' EXTRACELLULAR DOMAINS OF CLONE Hu-B1.219

```
..C...C..........C....C..............PP.V.......W.....Y..........P...Y..R...G.WSNWS..
  (11)     (41)     (10)          (41)     (3)  (15)   (16)     (27)    (6) (5)(8)(2)
```

FIG.4

```
                           * . * . * .
mIL2Rβ         E P Y L E F E A R R R L L
hIL2Rγ         E H L V Q Y R T D W D H S
mIL5Rα         D H C F N Y E L K I Y N T
mEPOR          T T H I R Y E V D V S A G
Hu-B1.219(5')  P F P L Q Y Q V K Y Q V K
Hu-B1.219(3')  Q F Q I R Y G L S G K E V

HYDROPHOBIC:   "*"
HYDROPHILIC:   "-"
```

FIG.5

```
                           * b * b * b
mIL-2Rβ        S T S Y E V Q V R V K A Q R N
hIL-2Rγ        Q K R Y T F R V R S R F N P L
mIL-5Rα        L S K Y D V Q V R A A V S S M
mEPOR          G T R Y T F A V R A R M A P S
Hu-B1.219(5')  G S S Y E V Q V R G K R L D G
Hu-B1.219(3')  C A V Y A V Q V R C K R L D G
                       Y           R

HYDROPHOBIC:   "*"
BASIC:         "b"
```

FIG.6

```
                         SEQUENCE LISTING

<160> NUMBER OF SEQ ID NOS:  33

<210> SEQ ID NO 1
<211> LENGTH: 5
<212> TYPE: PRT
<213> ORGANISM: Homo sapiens
<220> FEATURE:
<221> NAME/KEY: SITE
<222> LOCATION: 3
<223> OTHER INFORMATION: Xaa = any amino acid

<400> SEQUENCE: 1

Trp Ser Xaa Trp Ser
 1               5

<210> SEQ ID NO 2
<211> LENGTH: 18
<212> TYPE: DNA
<213> ORGANISM: Homo sapiens

<400> SEQUENCE: 2
ggtttgcata tggaagtc                                                   18

<210> SEQ ID NO 3
<211> LENGTH: 19
<212> TYPE: DNA
<213> ORGANISM: Homo sapiens

<400> SEQUENCE: 3
cctgaaccat ccagtctct                                                  19

<210> SEQ ID NO 4
<211> LENGTH: 21
<212> TYPE: DNA
<213> ORGANISM: Homo sapiens

<400> SEQUENCE: 4
gactcattgt gcagtgttca g                                               21

<210> SEQ ID NO 5
<211> LENGTH: 21
<212> TYPE: DNA
<213> ORGANISM: Homo sapiens

<400> SEQUENCE: 5
tagtggaggg agggtcagca g                                               21
```

<210> SEQ ID NO 6
<211> LENGTH: 2991
<212> TYPE: DNA
<213> ORGANISM: Homo sapiens
<220> FEATURE:
<221> NAME/KEY: CDS
<222> LOCATION: (1)...(2991)

<400> SEQUENCE: 6

| | |
|---|---|
| gcg cgc gcg acg cag gtg ccc gag ccc cgg ccc gcg ccc atc tct gcc<br>Ala Arg Ala Thr Gln Val Pro Glu Pro Arg Pro Ala Pro Ile Ser Ala<br>1                  5                    10                15 | 48 |
| ttc ggt cga gtt gga ccc ccg gat caa ggt gta ctt ctc tga agt aag<br>Phe Gly Arg Val Gly Pro Pro Asp Gln Gly Val Leu Leu        Ser Lys<br>              20                    25                    30 | 96 |
| atg att tgt caa aaa ttc tgt gtg gtt ttg tta cat tgg gaa ttt att<br>Met Ile Cys Gln Lys Phe Cys Val Val Leu Leu His Trp Glu Phe Ile<br>            35                    40                    45 | 144 |
| tat gtg ata act gcg ttt aac ttg tca tat cca att act cct tgg aga<br>Tyr Val Ile Thr Ala Phe Asn Leu Ser Tyr Pro Ile Thr Pro Trp Arg<br>50                    55                    60 | 192 |
| ttt aag ttg tct tgc atg cca cca aat tca acc tat gac tac ttc ctt<br>Phe Lys Leu Ser Cys Met Pro Pro Asn Ser Thr Tyr Asp Tyr Phe Leu<br>65                    70                    75 | 240 |
| ttg cct gct gga ctc tca aag aat act tca aat tcg aat gga cat tat<br>Leu Pro Ala Gly Leu Ser Lys Asn Thr Ser Asn Ser Asn Gly His Tyr<br>80                    85                    90                    95 | 288 |
| gag aca gct gtt gaa cct aag ttt aat tca agt ggt act cac ttt tct<br>Glu Thr Ala Val Glu Pro Lys Phe Asn Ser Ser Gly Thr His Phe Ser<br>                    100                   105                  110 | 336 |
| aac tta tcc aaa gca act ttc cac tgt tgc ttt cgg agt gag caa gat<br>Asn Leu Ser Lys Ala Thr Phe His Cys Cys Phe Arg Ser Glu Gln Asp<br>              115                    120                    125 | 384 |
| aga aac tgc tcc tta tgt gca gac aac att gaa gga agg aca ttt gtt<br>Arg Asn Cys Ser Leu Cys Ala Asp Asn Ile Glu Gly Arg Thr Phe Val<br>            130                    135                    140 | 432 |
| tca aca gta aat tct tta gtt ttt caa caa ata gat gca aac tgg aac<br>Ser Thr Val Asn Ser Leu Val Phe Gln Gln Ile Asp Ala Asn Trp Asn<br>145                  150                    155 | 480 |
| ata cag tgc tgg cta aaa gga gac tta aaa tta ttc atc tgt tat gtg<br>Ile Gln Cys Trp Leu Lys Gly Asp Leu Lys Leu Phe Ile Cys Tyr Val<br>160                  165                    170                    175 | 528 |
| gag tca tta ttt aag aat cta ttc agg aat tat aac tat aag gtc cat<br>Glu Ser Leu Phe Lys Asn Leu Phe Arg Asn Tyr Asn Tyr Lys Val His<br>                    180                    185                  190 | 576 |
| ctt tta tat gtt ctg cct gaa gtg tta gaa gat tca cct ctg gtt ccc<br>Leu Leu Tyr Val Leu Pro Glu Val Leu Glu Asp Ser Pro Leu Val Pro<br>              195                    200                    205 | 624 |
| caa aaa ggc agt ttt cag atg gtt cac tgc aat tgc agt gtt cat gaa<br>Gln Lys Gly Ser Phe Gln Met Val His Cys Asn Cys Ser Val His Glu<br>            210                    215                    220 | 672 |
| tgt tgt gaa tgt ctt gtg cct gtg cca aca gcc aaa ctc aac gac act<br>Cys Cys Glu Cys Leu Val Pro Val Pro Thr Ala Lys Leu Asn Asp Thr<br>225                  230                    235 | 720 |
| ctc ctt atg tgt ttg aaa atc aca tct ggt gga gta att ttc cgg tca<br>Leu Leu Met Cys Leu Lys Ile Thr Ser Gly Gly Val Ile Phe Arg Ser<br>240                  245                    250                    255 | 768 |
| cct cta atg tca gtt cag ccc ata aat atg gtg aag cct gat cca cca<br>Pro Leu Met Ser Val Gln Pro Ile Asn Met Val Lys Pro Asp Pro Pro<br>                    260                    265                  270 | 816 |

-continued

```
tta ggt ttg cat atg gaa atc aca gat gat ggt aat tta aag att tct      864
Leu Gly Leu His Met Glu Ile Thr Asp Asp Gly Asn Leu Lys Ile Ser
            275                 280                 285 tgg tcc agc cca cca ttg gta cca ttt cca ctt caa tat caa gtg aaa      912
Trp Ser Ser Pro Pro Leu Val Pro Phe Pro Leu Gln Tyr Gln Val Lys
        290                 295                 300 tat tca gag aat tct aca aca gtt atc aga gaa gct gac aag att gtc      960
Tyr Ser Glu Asn Ser Thr Thr Val Ile Arg Glu Ala Asp Lys Ile Val
    305                 310                 315 tca gct aca tcc ctg cta gta gac agt ata ctt cct ggg tct tcg tat     1008
Ser Ala Thr Ser Leu Leu Val Asp Ser Ile Leu Pro Gly Ser Ser Tyr
320                 325                 330                 335 gag gtt cag gtg agg ggc aag aga ctg gat ggc cca gga atc tgg agt     1056
Glu Val Gln Val Arg Gly Lys Arg Leu Asp Gly Pro Gly Ile Trp Ser
                340                 345                 350 gac tgg agt act cct cgt gtc ttt acc aca caa gat gtc ata tac ttt     1104
Asp Trp Ser Thr Pro Arg Val Phe Thr Thr Gln Asp Val Ile Tyr Phe
            355                 360                 365 cca cct aaa att ctg aca agt gtt ggg tct aat gtt tct ttt cac tgc     1152
Pro Pro Lys Ile Leu Thr Ser Val Gly Ser Asn Val Ser Phe His Cys
        370                 375                 380 atc tat aag aag gaa aac aag att gtt ccc tca aaa gag att gtt tgg     1200
Ile Tyr Lys Lys Glu Asn Lys Ile Val Pro Ser Lys Glu Ile Val Trp
    385                 390                 395 tgg atg aat tta gct gag aaa att cct caa agc cag tat gat gtt gtg     1248
Trp Met Asn Leu Ala Glu Lys Ile Pro Gln Ser Gln Tyr Asp Val Val
400                 405                 410                 415 agt gat cat gtt agc aaa gtt act ttt ttc aat ctg aat gaa acc aaa     1296
Ser Asp His Val Ser Lys Val Thr Phe Phe Asn Leu Asn Glu Thr Lys
                420                 425                 430 cct cga gga aag ttt acc tat gat gca gtg tac tgc tgc aat gaa cat     1344
Pro Arg Gly Lys Phe Thr Tyr Asp Ala Val Tyr Cys Cys Asn Glu His
            435                 440                 445 gaa tgc cat cat cgc tat gct gaa tta tat gtg att gat gtc aat atc     1392
Glu Cys His His Arg Tyr Ala Glu Leu Tyr Val Ile Asp Val Asn Ile
        450                 455                 460 aat atc tca tgt gaa act gat ggg tac tta act aaa atg act tgc aga     1440
Asn Ile Ser Cys Glu Thr Asp Gly Tyr Leu Thr Lys Met Thr Cys Arg
    465                 470                 475 tgg tca acc agt aca atc cag tca ctt gcg gaa agc act ttg caa ttg     1488
Trp Ser Thr Ser Thr Ile Gln Ser Leu Ala Glu Ser Thr Leu Gln Leu
480                 485                 490                 495 agg tat cat agg agc agc ctt tac tgt tct gat att cca tct att cat     1536
Arg Tyr His Arg Ser Ser Leu Tyr Cys Ser Asp Ile Pro Ser Ile His
                500                 505                 510 ccc ata tct gag ccc aaa gat tgc tat ttg cag agt gat ggt ttt tat     1584
Pro Ile Ser Glu Pro Lys Asp Cys Tyr Leu Gln Ser Asp Gly Phe Tyr
            515                 520                 525 gaa tgc att ttc cag cca atc ttc cta tta tct ggc tac aca atg tgg     1632
Glu Cys Ile Phe Gln Pro Ile Phe Leu Leu Ser Gly Tyr Thr Met Trp
        530                 535                 540 att agg atc aat cac tct cta ggt tca ctt gac tct cca cca aca tgt     1680
Ile Arg Ile Asn His Ser Leu Gly Ser Leu Asp Ser Pro Pro Thr Cys
    545                 550                 555 gtc ctt cct gat tct gtg gtg aag cca ctg cct cca tcc agt gtg aaa     1728
Val Leu Pro Asp Ser Val Val Lys Pro Leu Pro Pro Ser Ser Val Lys
560                 565                 570                 575 gca gaa att act ata aac att gga tta ttg aaa ata tct tgg gaa aag     1776
Ala Glu Ile Thr Ile Asn Ile Gly Leu Leu Lys Ile Ser Trp Glu Lys
```

-continued

```
                 580                 585                 590
cca gtc ttt cca gag aat aac ctt caa ttc cag att cgc tat ggt tta    1824
Pro Val Phe Pro Glu Asn Asn Leu Gln Phe Gln Ile Arg Tyr Gly Leu
            595                 600                 605 agt gga aaa gaa gta caa tgg aag atg tat gag gtt tat gat gca aaa    1872
Ser Gly Lys Glu Val Gln Trp Lys Met Tyr Glu Val Tyr Asp Ala Lys
        610                 615                 620 tca aaa tct gtc agt ctc cca gtt cca gac ttg tgt gca gtc tat gct    1920
Ser Lys Ser Val Ser Leu Pro Val Pro Asp Leu Cys Ala Val Tyr Ala
    625                 630                 635 gtt cag gtg cgc tgt aag agg cta gat gga ctg gga tat tgg agt aat    1968
Val Gln Val Arg Cys Lys Arg Leu Asp Gly Leu Gly Tyr Trp Ser Asn
640                 645                 650                 655 tgg agc aat cca gcc tac aca gtt gtc atg gat ata aaa gtt cct atg    2016
Trp Ser Asn Pro Ala Tyr Thr Val Val Met Asp Ile Lys Val Pro Met
                660                 665                 670 aga gga cct gaa ttt tgg aga ata att aat gga gat act atg aaa aag    2064
Arg Gly Pro Glu Phe Trp Arg Ile Ile Asn Gly Asp Thr Met Lys Lys
            675                 680                 685 gag aaa aat gtc act tta ctt tgg aag ccc ctg atg aaa aat gac tca    2112
Glu Lys Asn Val Thr Leu Leu Trp Lys Pro Leu Met Lys Asn Asp Ser
        690                 695                 700 ttg tgc agt gtt cag aga tat gtg ata aac cat cat act tcc tgc aat    2160
Leu Cys Ser Val Gln Arg Tyr Val Ile Asn His His Thr Ser Cys Asn
    705                 710                 715 gga aca tgg tca gaa gat gtg gga aat cac acg aaa ttc act ttc ctg    2208
Gly Thr Trp Ser Glu Asp Val Gly Asn His Thr Lys Phe Thr Phe Leu
720                 725                 730                 735 tgg aca gag caa gca cat act gtt acg gtt ctg gcc atc aat tca att    2256
Trp Thr Glu Gln Ala His Thr Val Thr Val Leu Ala Ile Asn Ser Ile
                740                 745                 750 ggt gct tct gtt gca aat ttt aat tta acc ttt tca tgg cct atg agc    2304
Gly Ala Ser Val Ala Asn Phe Asn Leu Thr Phe Ser Trp Pro Met Ser
            755                 760                 765 aaa gta aat atc gtg cag tca ctc agt gct tat cct tta aac agc agt    2352
Lys Val Asn Ile Val Gln Ser Leu Ser Ala Tyr Pro Leu Asn Ser Ser
        770                 775                 780 tgt gtg att gtt tcc tgg ata cta tca ccc agt gat tac aag cta atg    2400
Cys Val Ile Val Ser Trp Ile Leu Ser Pro Ser Asp Tyr Lys Leu Met
    785                 790                 795 tat ttt att att gag tgg aaa aat ctt aat gaa gat ggt gaa ata aaa    2448
Tyr Phe Ile Ile Glu Trp Lys Asn Leu Asn Glu Asp Gly Glu Ile Lys
800                 805                 810                 815 tgg ctt aga atc tct tca tct gtt aag aag tat tat atc cat gat cat    2496
Trp Leu Arg Ile Ser Ser Ser Val Lys Lys Tyr Tyr Ile His Asp His
                820                 825                 830 ttt atc ccc att gag aag tac cag ttc agt ctt tac cca ata ttt atg    2544
Phe Ile Pro Ile Glu Lys Tyr Gln Phe Ser Leu Tyr Pro Ile Phe Met
            835                 840                 845 gaa gga gtg gga aaa cca aag ata att aat agt ttc act caa gat gat    2592
Glu Gly Val Gly Lys Pro Lys Ile Ile Asn Ser Phe Thr Gln Asp Asp
        850                 855                 860 att gaa aaa cac cag agt gat gca ggt tta tat gta att gtg cca gta    2640
Ile Glu Lys His Gln Ser Asp Ala Gly Leu Tyr Val Ile Val Pro Val
    865                 870                 875 att att tcc tct tcc atc tta ttg ctt gga aca tta tta ata tca cac    2688
Ile Ile Ser Ser Ser Ile Leu Leu Leu Gly Thr Leu Leu Ile Ser His
880                 885                 890                 895 caa aga atg aaa aag cta ttt tgg gaa gat gtt ccg aac ccc aag aat    2736
```

```
Gln Arg Met Lys Lys Leu Phe Trp Glu Asp Val Pro Asn Pro Lys Asn
                900                 905                 910 tgt tcc tgg gca caa gga ctt aat ttt cag aag atg ctt gaa ggc agc      2784
Cys Ser Trp Ala Gln Gly Leu Asn Phe Gln Lys Met Leu Glu Gly Ser
            915                 920                 925 atg ttc gtt aag agt cat cac cac tcc cta atc tca agt acc cag gga      2832
Met Phe Val Lys Ser His His His Ser Leu Ile Ser Ser Thr Gln Gly
        930                 935                 940 cac aaa cac tgc gga agg cca cag ggt cct ctg cat agg aaa acc aga      2880
His Lys His Cys Gly Arg Pro Gln Gly Pro Leu His Arg Lys Thr Arg
    945                 950                 955 gac ctt tgt tca ctt gtt tat ctg ctg acc ctc cct cca cta ttg tcc      2928
Asp Leu Cys Ser Leu Val Tyr Leu Leu Thr Leu Pro Pro Leu Leu Ser
960                 965                 970                 975 tat gac cct gcc aaa tcc ccc tct gtg aga aac acc caa gaa tga tca      2976
Tyr Asp Pro Ala Lys Ser Pro Ser Val Arg Asn Thr Gln Glu  *  Ser
                980                 985                     990 ata aaa aaa aaa aaa                                                  2991
Ile Lys Lys Lys Lys
                995

<210> SEQ ID NO 7
<211> LENGTH: 29
<212> TYPE: PRT
<213> ORGANISM: Homo sapiens

<400> SEQUENCE: 7

Ala Arg Ala Thr Gln Val Pro Glu Pro Arg Pro Ala Pro Ile Ser Ala
1               5                   10                  15

Phe Gly Arg Val Gly Pro Pro Asp Gln Gly Val Leu Leu
            20                  25

<210> SEQ ID NO 8
<211> LENGTH: 960
<212> TYPE: PRT
<213> ORGANISM: Homo sapiens

<400> SEQUENCE: 8

Ser Lys Met Ile Cys Gln Lys Phe Cys Val Val Leu Leu His Trp Glu
1               5                   10                  15

Phe Ile Tyr Val Ile Thr Ala Phe Asn Leu Ser Tyr Pro Ile Thr Pro
            20                  25                  30

Trp Arg Phe Lys Leu Ser Cys Met Pro Pro Asn Ser Thr Tyr Asp Tyr
        35                  40                  45

Phe Leu Leu Pro Ala Gly Leu Ser Lys Asn Thr Ser Asn Ser Asn Gly
    50                  55                  60

His Tyr Glu Thr Ala Val Glu Pro Lys Phe Asn Ser Ser Gly Thr His
65                  70                  75                  80

Phe Ser Asn Leu Ser Lys Ala Thr Phe His Cys Cys Phe Arg Ser Glu
                85                  90                  95

Gln Asp Arg Asn Cys Ser Leu Cys Ala Asp Asn Ile Glu Gly Arg Thr
            100                 105                 110

Phe Val Ser Thr Val Asn Ser Leu Val Phe Gln Gln Ile Asp Ala Asn
        115                 120                 125

Trp Asn Ile Gln Cys Trp Leu Lys Gly Asp Leu Lys Leu Phe Ile Cys
    130                 135                 140

Tyr Val Glu Ser Leu Phe Lys Asn Leu Phe Arg Asn Tyr Asn Tyr Lys
145                 150                 155                 160
```

-continued

Val His Leu Leu Tyr Val Leu Pro Glu Val Leu Glu Asp Ser Pro Leu
                165                 170                 175

Val Pro Gln Lys Gly Ser Phe Gln Met Val His Cys Asn Cys Ser Val
                180                 185                 190

His Glu Cys Cys Glu Cys Leu Val Pro Val Pro Thr Ala Lys Leu Asn
                195                 200                 205

Asp Thr Leu Leu Met Cys Leu Lys Ile Thr Ser Gly Gly Val Ile Phe
210                 215                 220

Arg Ser Pro Leu Met Ser Val Gln Pro Ile Asn Met Val Lys Pro Asp
225                 230                 235                 240

Pro Pro Leu Gly Leu His Met Glu Ile Thr Asp Asp Gly Asn Leu Lys
                245                 250                 255

Ile Ser Trp Ser Ser Pro Pro Leu Val Pro Phe Pro Leu Gln Tyr Gln
                260                 265                 270

Val Lys Tyr Ser Glu Asn Ser Thr Thr Val Ile Arg Glu Ala Asp Lys
                275                 280                 285

Ile Val Ser Ala Thr Ser Leu Leu Val Asp Ser Ile Leu Pro Gly Ser
290                 295                 300

Ser Tyr Glu Val Gln Val Arg Gly Lys Arg Leu Asp Gly Pro Gly Ile
305                 310                 315                 320

Trp Ser Asp Trp Ser Thr Pro Arg Val Phe Thr Thr Gln Asp Val Ile
                325                 330                 335

Tyr Phe Pro Pro Lys Ile Leu Thr Ser Val Gly Ser Asn Val Ser Phe
                340                 345                 350

His Cys Ile Tyr Lys Lys Glu Asn Lys Ile Val Pro Ser Lys Glu Ile
                355                 360                 365

Val Trp Trp Met Asn Leu Ala Glu Lys Ile Pro Gln Ser Gln Tyr Asp
                370                 375                 380

Val Val Ser Asp His Val Ser Lys Val Thr Phe Phe Asn Leu Asn Glu
385                 390                 395                 400

Thr Lys Pro Arg Gly Lys Phe Thr Tyr Asp Ala Val Tyr Cys Cys Asn
                405                 410                 415

Glu His Glu Cys His His Arg Tyr Ala Glu Leu Tyr Val Ile Asp Val
                420                 425                 430

Asn Ile Asn Ile Ser Cys Glu Thr Asp Gly Tyr Leu Thr Lys Met Thr
                435                 440                 445

Cys Arg Trp Ser Thr Ser Thr Ile Gln Ser Leu Ala Glu Ser Thr Leu
450                 455                 460

Gln Leu Arg Tyr His Arg Ser Ser Leu Tyr Cys Ser Asp Ile Pro Ser
465                 470                 475                 480

Ile His Pro Ile Ser Glu Pro Lys Asp Cys Tyr Leu Gln Ser Asp Gly
                485                 490                 495

Phe Tyr Glu Cys Ile Phe Gln Pro Ile Phe Leu Leu Ser Gly Tyr Thr
                500                 505                 510

Met Trp Ile Arg Ile Asn His Ser Leu Gly Ser Leu Asp Ser Pro Pro
                515                 520                 525

Thr Cys Val Leu Pro Asp Ser Val Val Lys Pro Leu Pro Pro Ser Ser
530                 535                 540

Val Lys Ala Glu Ile Thr Ile Asn Ile Gly Leu Leu Lys Ile Ser Trp
545                 550                 555                 560

Glu Lys Pro Val Phe Pro Glu Asn Asn Leu Gln Phe Gln Ile Arg Tyr
                565                 570                 575

Gly Leu Ser Gly Lys Glu Val Gln Trp Lys Met Tyr Glu Val Tyr Asp

```
              580             585             590
Ala Lys Ser Lys Ser Val Ser Leu Pro Val Pro Asp Leu Cys Ala Val
            595             600             605
Tyr Ala Val Gln Val Arg Cys Lys Arg Leu Asp Gly Leu Gly Tyr Trp
610             615             620
Ser Asn Trp Ser Asn Pro Ala Tyr Thr Val Val Met Asp Ile Lys Val
625             630             635             640
Pro Met Arg Gly Pro Glu Phe Trp Arg Ile Ile Asn Gly Asp Thr Met
            645             650             655
Lys Lys Glu Lys Asn Val Thr Leu Leu Trp Lys Pro Leu Met Lys Asn
            660             665             670
Asp Ser Leu Cys Ser Val Gln Arg Tyr Val Ile Asn His His Thr Ser
            675             680             685
Cys Asn Gly Thr Trp Ser Glu Asp Val Gly Asn His Thr Lys Phe Thr
690             695             700
Phe Leu Trp Thr Glu Gln Ala His Thr Val Thr Val Leu Ala Ile Asn
705             710             715             720
Ser Ile Gly Ala Ser Val Ala Asn Phe Asn Leu Thr Phe Ser Trp Pro
            725             730             735
Met Ser Lys Val Asn Ile Val Gln Ser Leu Ser Ala Tyr Pro Leu Asn
            740             745             750
Ser Ser Cys Val Ile Val Ser Trp Ile Leu Ser Pro Ser Asp Tyr Lys
            755             760             765
Leu Met Tyr Phe Ile Ile Glu Trp Lys Asn Leu Asn Glu Asp Gly Glu
            770             775             780
Ile Lys Trp Leu Arg Ile Ser Ser Val Lys Lys Tyr Tyr Ile His
785             790             795             800
Asp His Phe Ile Pro Ile Glu Lys Tyr Gln Phe Ser Leu Tyr Pro Ile
            805             810             815
Phe Met Glu Gly Val Gly Lys Pro Lys Ile Ile Asn Ser Phe Thr Gln
            820             825             830
Asp Asp Ile Glu Lys His Gln Ser Asp Ala Gly Leu Tyr Val Ile Val
            835             840             845
Pro Val Ile Ile Ser Ser Ser Ile Leu Leu Leu Gly Thr Leu Leu Ile
850             855             860
Ser His Gln Arg Met Lys Lys Leu Phe Trp Glu Asp Val Pro Asn Pro
865             870             875             880
Lys Asn Cys Ser Trp Ala Gln Gly Leu Asn Phe Gln Lys Met Leu Glu
            885             890             895
Gly Ser Met Phe Val Lys Ser His His His Ser Leu Ile Ser Ser Thr
            900             905             910
Gln Gly His Lys His Cys Gly Arg Pro Gln Gly Pro Leu His Arg Lys
            915             920             925
Thr Arg Asp Leu Cys Ser Leu Val Tyr Leu Leu Thr Leu Pro Pro Leu
            930             935             940
Leu Ser Tyr Asp Pro Ala Lys Ser Pro Ser Val Arg Asn Thr Gln Glu
945             950             955             960

<210> SEQ ID NO 9
<211> LENGTH: 6
<212> TYPE: PRT
<213> ORGANISM: Homo sapiens

<400> SEQUENCE: 9
```

Ser Ile Lys Lys Lys Lys
1               5

<210> SEQ ID NO 10
<211> LENGTH: 241
<212> TYPE: DNA
<213> ORGANISM: Homo sapiens
<220> FEATURE:
<221> NAME/KEY: CDS
<222> LOCATION: (2)...(241)

<400> SEQUENCE: 10

```
a gga ctt aat ttt cag aag atg ctt gaa ggc agc atg ttc gtt aag agt    49
  Gly Leu Asn Phe Gln Lys Met Leu Glu Gly Ser Met Phe Val Lys Ser
  1               5                  10                  15 cat cac cac tcc cta atc tca agt acc cag gga cac aaa cac tgc gga      97
His His His Ser Leu Ile Ser Ser Thr Gln Gly His Lys His Cys Gly
            20                  25                  30 agg cca cag ggt cct ctg cat agg aaa acc aga gac ctt tgt tca ctt      145
Arg Pro Gln Gly Pro Leu His Arg Lys Thr Arg Asp Leu Cys Ser Leu
        35                  40                  45 gtt tat ctg ctg acc ctc cct cca cta ttg tcc tat gac cct gcc aaa      193
Val Tyr Leu Leu Thr Leu Pro Pro Leu Leu Ser Tyr Asp Pro Ala Lys
50                  55                  60 tcc ccc tct gtg aga aac acc caa gaa tga tca ata aaa aaa aaa aaa      241
Ser Pro Ser Val Arg Asn Thr Gln Glu     Ser Ile Lys Lys Lys Lys
65                  70                      75
```

<210> SEQ ID NO 11
<211> LENGTH: 73
<212> TYPE: PRT
<213> ORGANISM: Homo sapiens

<400> SEQUENCE: 11

Gly Leu Asn Phe Gln Lys Met Leu Glu Gly Ser Met Phe Val Lys Ser
1               5                   10                  15

His His His Ser Leu Ile Ser Ser Thr Gln Gly His Lys His Cys Gly
            20                  25                  30

Arg Pro Gln Gly Pro Leu His Arg Lys Thr Arg Asp Leu Cys Ser Leu
        35                  40                  45

Val Tyr Leu Leu Thr Leu Pro Pro Leu Leu Ser Tyr Asp Pro Ala Lys
    50                  55                  60

Ser Pro Ser Val Arg Asn Thr Gln Glu
65                  70

<210> SEQ ID NO 12
<211> LENGTH: 6
<212> TYPE: PRT
<213> ORGANISM: Homo sapiens

<400> SEQUENCE: 12

Ser Ile Lys Lys Lys Lys
1               5

<210> SEQ ID NO 13
<211> LENGTH: 130
<212> TYPE: DNA
<213> ORGANISM: Homo sapiens
<220> FEATURE:
<221> NAME/KEY: CDS
<222> LOCATION: (2)...(130)

<400> SEQUENCE: 13

```
a gga ctt aat ttt cag aag aaa atg cct ggc aca aag gaa cta ctg ggt      49
  Gly Leu Asn Phe Gln Lys Lys Met Pro Gly Thr Lys Glu Leu Leu Gly
   1               5                  10                  15
gga ggt tgg ttg act tag gaa atg ctt gtg aag cta cgt cct acc tcg        97
Gly Gly Trp Leu Thr     Glu Met Leu Val Lys Leu Arg Pro Thr Ser
             20                      25                  30
tgc gca cct gct ctc cct gag gtg tgc aca atg                            130
Cys Ala Pro Ala Leu Pro Glu Val Cys Thr Met
             35                  40
```

<210> SEQ ID NO 14
<211> LENGTH: 21
<212> TYPE: PRT
<213> ORGANISM: Homo sapiens

<400> SEQUENCE: 14

```
Gly Leu Asn Phe Gln Lys Lys Met Pro Gly Thr Lys Glu Leu Leu Gly
 1               5                  10                  15
Gly Gly Trp Leu Thr
             20
```

<210> SEQ ID NO 15
<211> LENGTH: 21
<212> TYPE: PRT
<213> ORGANISM: Homo sapiens

<400> SEQUENCE: 15

```
Glu Met Leu Val Lys Leu Arg Pro Thr Ser Cys Ala Pro Ala Leu Pro
 1               5                  10                  15
Glu Val Cys Thr Met
             20
```

<210> SEQ ID NO 16
<211> LENGTH: 127
<212> TYPE: DNA
<213> ORGANISM: Homo sapiens
<220> FEATURE:
<221> NAME/KEY: CDS
<222> LOCATION: (2)...(127)

<400> SEQUENCE: 16

```
a gga ctt aat ttt cag aag aga acg gac att ctt tga agt cta atc atg     49
  Gly Leu Asn Phe Gln Lys Arg Thr Asp Ile Leu  *  Ser Leu Ile Met
   1               5                  10                  15
atc act aca gat gaa ccc aat gtg cca act tcc caa cag tct ata gag       97
Ile Thr Thr Asp Glu Pro Asn Val Pro Thr Ser Gln Gln Ser Ile Glu
             20                      25                  30
tat tag aag att ttt aca ttc tga aga agg                               127
Tyr  *  Lys Ile Phe Thr Phe  *  Arg Arg
             35
```

<210> SEQ ID NO 17
<211> LENGTH: 11
<212> TYPE: PRT
<213> ORGANISM: Homo sapiens

<400> SEQUENCE: 17

```
Gly Leu Asn Phe Gln Lys Arg Thr Asp Ile Leu
 1               5                  10
```

<210> SEQ ID NO 18
<211> LENGTH: 21
<212> TYPE: PRT
<213> ORGANISM: Homo sapiens

<400> SEQUENCE: 18

```
Ser Leu Ile Met Ile Thr Thr Asp Glu Pro Asn Val Pro Thr Ser Gln
1               5                   10                  15

Gln Ser Ile Glu Tyr
            20
```

<210> SEQ ID NO 19
<211> LENGTH: 5
<212> TYPE: PRT
<213> ORGANISM: Homo sapiens

<400> SEQUENCE: 19

```
Lys Ile Phe Thr Phe
1               5
```

<210> SEQ ID NO 20
<211> LENGTH: 13
<212> TYPE: PRT
<213> ORGANISM: Homo sapiens

<400> SEQUENCE: 20

```
Glu Pro Tyr Leu Glu Phe Glu Ala Arg Arg Arg Leu Leu
1               5                   10
```

<210> SEQ ID NO 21
<211> LENGTH: 13
<212> TYPE: PRT
<213> ORGANISM: Homo sapiens

<400> SEQUENCE: 21

```
Glu His Leu Val Gln Tyr Arg Thr Asp Trp Asp His Ser
1               5                   10
```

<210> SEQ ID NO 22
<211> LENGTH: 13
<212> TYPE: PRT
<213> ORGANISM: Homo sapiens

<400> SEQUENCE: 22

```
Asp His Cys Phe Asn Tyr Glu Leu Lys Ile Tyr Asn Thr
1               5                   10
```

<210> SEQ ID NO 23
<211> LENGTH: 13
<212> TYPE: PRT
<213> ORGANISM: Homo sapiens

<400> SEQUENCE: 23

```
Thr Thr His Ile Arg Tyr Glu Val Asp Val Ser Ala Gly
1               5                   10
```

<210> SEQ ID NO 24
<211> LENGTH: 13
<212> TYPE: PRT
<213> ORGANISM: Homo sapiens

<400> SEQUENCE: 24

```
Pro Phe Pro Leu Gln Tyr Gln Val Lys Tyr Gln Val Lys
1               5                   10
```

<210> SEQ ID NO 25
<211> LENGTH: 13
<212> TYPE: PRT
<213> ORGANISM: Homo sapiens

```
<400> SEQUENCE: 25

Gln Phe Gln Ile Arg Tyr Gly Leu Ser Gly Lys Glu Val
 1               5                  10

<210> SEQ ID NO 26
<211> LENGTH: 15
<212> TYPE: PRT
<213> ORGANISM: Homo sapiens

<400> SEQUENCE: 26

Ser Thr Ser Tyr Glu Val Gln Val Arg Val Lys Ala Gln Arg Asn
 1               5                  10                  15

<210> SEQ ID NO 27
<211> LENGTH: 15
<212> TYPE: PRT
<213> ORGANISM: Homo sapiens

<400> SEQUENCE: 27

Gln Lys Arg Tyr Thr Phe Arg Val Arg Ser Arg Phe Asn Pro Leu
 1               5                  10                  15

<210> SEQ ID NO 28
<211> LENGTH: 15
<212> TYPE: PRT
<213> ORGANISM: Homo sapiens

<400> SEQUENCE: 28

Leu Ser Lys Tyr Asp Val Gln Val Arg Ala Ala Val Ser Ser Met
 1               5                  10                  15

<210> SEQ ID NO 29
<211> LENGTH: 15
<212> TYPE: PRT
<213> ORGANISM: Homo sapiens

<400> SEQUENCE: 29

Gly Thr Arg Tyr Thr Phe Ala Val Arg Ala Arg Met Ala Pro Ser
 1               5                  10                  15

<210> SEQ ID NO 30
<211> LENGTH: 15
<212> TYPE: PRT
<213> ORGANISM: Homo sapiens

<400> SEQUENCE: 30

Gly Ser Ser Tyr Glu Val Gln Val Arg Gly Lys Arg Leu Asp Gly
 1               5                  10                  15

<210> SEQ ID NO 31
<211> LENGTH: 15
<212> TYPE: PRT
<213> ORGANISM: Homo sapiens

<400> SEQUENCE: 31

Cys Ala Val Tyr Ala Val Gln Val Arg Cys Lys Arg Leu Asp Gly
 1               5                  10                  15

<210> SEQ ID NO 32
<211> LENGTH: 906
<212> TYPE: PRT
<213> ORGANISM: Homo sapiens

<400> SEQUENCE: 32
```

-continued

```
Met Ile Cys Gln Lys Phe Cys Val Val Leu Leu His Trp Glu Phe Ile
 1               5                  10                  15

Tyr Val Ile Thr Ala Phe Asn Leu Ser Tyr Pro Ile Thr Pro Trp Arg
             20                  25                  30

Phe Lys Leu Ser Cys Met Pro Pro Asn Ser Thr Tyr Asp Tyr Phe Leu
             35                  40                  45

Leu Pro Ala Gly Leu Ser Lys Asn Thr Ser Asn Ser Asn Gly His Tyr
     50                  55                  60

Glu Thr Ala Val Glu Pro Lys Phe Asn Ser Ser Gly Thr His Phe Ser
 65                  70                  75                  80

Asn Leu Ser Lys Ala Thr Phe His Cys Cys Phe Arg Ser Glu Gln Asp
                 85                  90                  95

Arg Asn Cys Ser Leu Cys Ala Asp Asn Ile Glu Gly Arg Thr Phe Val
            100                 105                 110

Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
    195                 200                 205

Leu Leu Met Cys Leu Lys Ile Thr Ser Gly Gly Val Ile Phe Arg Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
    275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
            325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
    355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
            405                 410                 415

Glu Cys His His Arg Tyr Ala Glu Leu Tyr Val Ile Asp Val Asn Ile
```

-continued

```
                420                  425                  430
Asn Ile Ser Cys Glu Thr Asp Gly Tyr Leu Thr Lys Met Thr Cys Arg
            435                  440                  445
Trp Ser Thr Ser Thr Ile Gln Ser Leu Ala Glu Ser Thr Leu Gln Leu
        450                  455                  460
Arg Tyr His Arg Ser Ser Leu Tyr Cys Ser Asp Ile Pro Ser Ile His
465                  470                  475                  480
Pro Ile Ser Glu Pro Lys Asp Cys Tyr Leu Gln Ser Asp Gly Phe Tyr
                485                  490                  495
Glu Cys Ile Phe Gln Pro Ile Phe Leu Leu Ser Gly Tyr Thr Met Trp
            500                  505                  510
Ile Arg Ile Asn His Ser Leu Gly Ser Leu Asp Ser Pro Pro Thr Cys
        515                  520                  525
Val Leu Pro Asp Ser Val Val Lys Pro Leu Pro Pro Ser Ser Val Lys
    530                  535                  540
Ala Glu Ile Thr Ile Asn Ile Gly Leu Leu Lys Ile Ser Trp Glu Lys
545                  550                  555                  560
Pro Val Phe Pro Glu Asn Asn Leu Gln Phe Gln Ile Arg Tyr Gly Leu
                565                  570                  575
Ser Gly Lys Glu Val Gln Trp Lys Met Tyr Glu Val Tyr Asp Ala Lys
            580                  585                  590
Ser Lys Ser Val Ser Leu Pro Val Pro Asp Leu Cys Ala Val Tyr Ala
        595                  600                  605
Val Gln Val Arg Cys Lys Arg Leu Asp Gly Leu Gly Tyr Trp Ser Asn
    610                  615                  620
Trp Ser Asn Pro Ala Tyr Thr Val Val Met Asp Ile Lys Val Pro Met
625                  630                  635                  640
Arg Gly Pro Glu Phe Trp Arg Ile Ile Asn Gly Asp Thr Met Lys Lys
                645                  650                  655
Glu Lys Asn Val Thr Leu Leu Trp Lys Pro Leu Met Lys Asn Asp Ser
            660                  665                  670
Leu Cys Ser Val Gln Arg Tyr Val Ile Asn His His Thr Ser Cys Asn
        675                  680                  685
Gly Thr Trp Ser Glu Asp Val Gly Asn His Thr Lys Phe Thr Phe Leu
    690                  695                  700
Trp Thr Glu Gln Ala His Thr Val Thr Val Leu Ala Ile Asn Ser Ile
705                  710                  715                  720
Gly Ala Ser Val Ala Asn Phe Asn Leu Thr Phe Ser Trp Pro Met Ser
                725                  730                  735
Lys Val Asn Ile Val Gln Ser Leu Ser Ala Tyr Pro Leu Asn Ser Ser
            740                  745                  750
Cys Val Ile Val Ser Trp Ile Leu Ser Pro Ser Asp Tyr Lys Leu Met
        755                  760                  765
Tyr Phe Ile Ile Glu Trp Lys Asn Leu Asn Glu Asp Gly Glu Ile Lys
    770                  775                  780
Trp Leu Arg Ile Ser Ser Val Lys Lys Tyr Tyr Ile His Asp His Phe
785                  790                  795                  800
Phe Ile Pro Ile Glu Lys Tyr Gln Phe Ser Leu Tyr Pro Ile Phe Met
                805                  810                  815
Glu Gly Val Gly Lys Pro Lys Ile Ile Asn Ser Phe Thr Gln Asp Asp
            820                  825                  830
Ile Glu Lys His Gln Ser Asp Ala Gly Leu Tyr Val Ile Val Pro Val
        835                  840                  845
```

-continued

```
Ile Ile Ser Ser Ser Ile Leu Leu Gly Thr Leu Leu Ile Ser His
        850                 855                 860
Gln Arg Met Lys Lys Leu Phe Trp Glu Asp Val Pro Asn Pro Lys Asn
865                 870                 875                 880
Cys Ser Trp Ala Gln Gly Leu Asn Phe Gln Lys Lys Met Pro Gly Thr
                885                 890                 895
Lys Glu Leu Leu Gly Gly Gly Trp Leu Thr
                900                 905

<210> SEQ ID NO 33
<211> LENGTH: 896
<212> TYPE: PRT
<213> ORGANISM: Homo sapiens

<400> SEQUENCE: 33

Met Ile Cys Gln Lys Phe Cys Val Val Leu Leu His Trp Glu Phe Ile
1               5                   10                  15
Tyr Val Ile Thr Ala Phe Asn Leu Ser Tyr Pro Ile Thr Pro Trp Arg
                20                  25                  30
Phe Lys Leu Ser Cys Met Pro Pro Asn Ser Thr Tyr Asp Tyr Phe Leu
            35                  40                  45
Leu Pro Ala Gly Leu Ser Lys Asn Thr Ser Asn Ser Asn Gly His Tyr
        50                  55                  60
Glu Thr Ala Val Glu Pro Lys Phe Asn Ser Ser Gly Thr His Phe Ser
65                  70                  75                  80
Asn Leu Ser Lys Ala Thr Phe His Cys Cys Phe Arg Ser Glu Gln Asp
                85                  90                  95
Arg Asn Cys Ser Leu Cys Ala Asp Asn Ile Glu Gly Arg Thr Phe Val
            100                 105                 110
Ser Thr Val Asn Ser Leu Val Phe Gln Gln Ile Asp Ala Asn Trp Asn
        115                 120                 125
Ile Gln Cys Trp Leu Lys Gly Asp Leu Lys Leu Phe Ile Cys Tyr Val
    130                 135                 140
Glu Ser Leu Phe Lys Asn Leu Phe Arg Asn Tyr Asn Tyr Lys Val His
145                 150                 155                 160
Leu Leu Tyr Val Leu Pro Glu Val Leu Glu Asp Ser Pro Leu Val Pro
                165                 170                 175
Gln Lys Gly Ser Phe Gln Met Val His Cys Asn Cys Ser Val His Glu
            180                 185                 190
Cys Cys Glu Cys Leu Val Pro Val Pro Thr Ala Lys Leu Asn Asp Thr
        195                 200                 205
Leu Leu Met Cys Leu Lys Ile Thr Ser Gly Gly Val Ile Phe Arg Ser
    210                 215                 220
Pro Leu Met Ser Val Gln Pro Ile Asn Met Val Lys Pro Asp Pro Pro
225                 230                 235                 240
Leu Gly Leu His Met Glu Ile Thr Asp Asp Gly Asn Leu Lys Ile Ser
                245                 250                 255
Trp Ser Ser Pro Pro Leu Val Pro Phe Pro Leu Gln Tyr Gln Val Lys
            260                 265                 270
Tyr Ser Glu Asn Ser Thr Thr Val Ile Arg Glu Ala Asp Lys Ile Val
        275                 280                 285
Ser Ala Thr Ser Leu Leu Val Asp Ser Ile Leu Pro Gly Ser Ser Tyr
    290                 295                 300
Glu Val Gln Val Arg Gly Lys Arg Leu Asp Gly Pro Gly Ile Trp Ser
```

```
                                         -continued 305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
                355                 360                 365

Trp Met Asn Leu Ala Glu Lys Ile Pro Gln Ser Gln Tyr Asp Val Val
        370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
                420                 425                 430

Asn Ile Ser Cys Glu Thr Asp Gly Tyr Leu Thr Lys Met Thr Cys Arg
            435                 440                 445

Trp Ser Thr Ser Thr Ile Gln Ser Leu Ala Glu Ser Thr Leu Gln Leu
        450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
                515                 520                 525

Val Leu Pro Asp Ser Val Val Lys Pro Leu Pro Pro Ser Ser Val Lys
        530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
        610                 615                 620

Trp Ser Asn Pro Ala Tyr Thr Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
        690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735
```

```
Lys Val Asn Ile Val Gln Ser Leu Ser Ala Tyr Pro Leu Asn Ser Ser
        740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Arg Thr Asp Ile Leu
                885                 890                 895
```

METHODS OF SCREENING FOR LIGANDS OF HUMAN HEMETOPOIETIN RECEPTOR HU-B1.219

This is a continuation of application Ser. No. 08/693,696, filed Aug. 5, 1996 (U.S. Pat. No. 6,005,080); which is a division of application Ser. No. 08/355,888, filed Dec. 14, 1994 (U.S. Pat. No. 5,763,211); which is a continuation-in-part of application Ser. No. 08/306,231, filed Sep. 14, 1994 (U.S. Pat. No. 5,643,748), which is incorporated by reference herein in its entirety.

TABLE OF CONTENTS

| TABLE OF CONTENTS | Page |
|---|---|
| 1. INTRODUCTION | 1 |
| 2. BACKGROUND OF THE INVENTION | 1 |
| 3. SUMMARY OF THE INVENTION | 3 |
| 4. BRIEF DESCRIPTION OF THE DRAWINGS | 4 |
| 5. DETAILED DESCRIPTION OF THE INVENTION | 5 |
|    5.1. THE Hu-B1.219 CODING SEQUENCE | 5 |
|    5.2. EXPRESSION OF Hu-B1.219 SEQUENCE | 7 |
|    5.3. EXPRESSION SYSTEMS | 10 |
|    5.4. IDENTIFICATION OF CELLS THAT EXPRESS Hu-B1.219 | 16 |
|    5.5. USES OF Hu-B1.219 ENGINEERED CELL LINES | 17 |
|    5.6. USES OF Hu-B1.219 POLYNUCLEOTIDE | 22 |
|       5.6.1. DIAGNOSTIC USES OF AN Hu-B1.219 POLYNUCLEOTIDE | 22 |
|       5.6.2. THERAPEUTIC USES OF AN Hu-B1.219 POLYNUCLEOTIDE | 22 |
| 6. EXAMPLE: MOLECULAR CLONING OF A NOVEL HEMATOPOIETIN RECEPTOR COMPLEMENTARY DNA | 25 |
|    6.1. MATERIALS AND METHODS | 25 |
|       6.1.1. NORTHERN BLOT ANALYSIS | 25 |
|       6.1.2. REVERSE TRANSCRIPTION/POLYMERASE CHAIN REACTION (RT/PCR) | 26 |
|    6.2. RESULTS | 26 |
| 7. Deposit of Microorganisms | 31 |

1. INTRODUCTION

The present invention relates to a novel member of the hematopoietin receptor family, herein referred to as Hu-B1.219. In particular, the invention relates to nucleotide sequences and expression vectors encoding Hu-B1.219 gene product. Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

2. BACKGROUND OF THE INVENTION

A variety of diseases, including malignancy and immunodeficiency, are related to malfunction within the lympho-hematopoietic system. Some of these conditions could be alleviated and/or cured by repopulating the hematopoietic system with progenitor cells, which when triggered to differentiate would overcome the patient's deficiency. Therefore, the ability to initiate and regulate hematopoiesis is of great importance (McCune et al., 1988, Science 241:1632).

The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors or cytokines (Metcalf, 1985, Science 229:16; Dexter, 1987, J. Cell Sci. 88:1; Golde and Gasson, 1988, Scientific American, July:62; Tabbara and Robinson, 1991, Anti-Cancer Res. 11:81; Ogawa, 1989, Environ. Health Presp. 80:199; Dexter, 1989, Er. Med. Bull. 45:337).

With the advent of recombinant DNA technology, the genes encoding a number of these molecules have now been molecularly cloned and expressed in recombinant form (Souza et al., 1986, Science 232:61; Gough et al., 1984, Nature 309:763; Yokota et al., 1984, Proc. Natl. Acad. Sci. U.S.A. 81:1070; Kawasaki et al., 1985, Science 230:291). These cytokines have been studied in their structure, biology and even therapeutic potential. Some of the most well characterized factors include erythropoietin (EPO), stem cell factor (SCF), granulocyte macrophage colony stimulating factor (GM-CSF), macrophage colony stimulating factor (M-CSF), granulocyte colony stimulating factor (G-CSF), and the interleukins (IL-1 to IL-14).

These factors act on different cell types at different stages during blood cell development, and their potential uses in medicine are far-reaching which include blood transfusions, bone marrow transplantation, correcting immunosuppressive disorders, cancer therapy, wound healing, and activation of the immune response. (Golde and Gasson, 1988, Scientific American, July:62).

Apart from inducing proliferation and differentiation of hematopoietic progenitor cells, such cytokines have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

Cytokines exert their effects on target cells by binding to specific cell surface receptors. A number of cytokine receptors have been identified and the genes encoding them molecularly cloned. Several cytokine receptors have recently been classified into a hematopoietin receptor (HR) superfamily. The grouping of these receptors was based on the conservation of key amino acid motifs in the extracellular domains (Bazan, 1990, Immunology Today 11:350) (FIG. 1). The HR family is defined by three conserved motifs in the extracellular domain of these receptors. The first is a Trp-Ser-X-Trp-Ser (WSXWS box) motif (SEQ ID NO:1) which is highly conserved and located amino-terminal to the transmembrane domain. Most members of the HR family contain this motif. The second consists of four conserved cysteine residues located in the amino-terminal half of the extracellular region. The third is a conserved fibronectin Type III (FN III) domain which is located between the WSXWS box and the cysteines. The members of the HR family include receptors for ligands such as erythropoietin (EPO), granulocyte colony stimulating factor (G-CSF) (Fukunaga, 1990, Cell 61:341), granulocyte-macrophage colony stimulating factor (GM-CSF), interleukin-3 (IL-3), IL-4, IL-5, IL-6, IL-7, and IL-2 (β-subunit) (Cosman, 1990, TIBS 15:265).

Ligands for the HR are critically involved in the maturation and differentiation of blood cells. For example, IL-3 promotes the proliferation of early multilineage pluripotent stem cells, and synergizes with EPO to produce red cells. IL-6 and IL-3 synergize to induce proliferation of early hematopoietic precursors. GM-CSF has been shown to induce the proliferation of granulocytes as well as increase macrophage function. IL-7 is a bone marrow-derived cytokine that plays a role in producing immature T and B lymphocytes. IL-4 induces proliferation of antigen-primed B cells and antigen-specific T cells. Thus, members of this receptor superfamily are involved in the regulation of the hematopoietic system.

3. SUMMARY OF THE INVENTION

The present invention relates to a novel member of the HR family, referred to as Hu-B1.219. In particular, it relates to the nucleotide sequences, expression vectors, host cells expressing the Hu-B1.219 gene, and proteins encoded by the sequences.

The invention is based, in part, upon Applicants' discovery of a cDNA clone, Hu-B1.219, isolated from a human fetal liver cDNA library. While the nucleotide sequence of this clone shares certain homology with other HR genes, it is also unique in its structure. Three forms of Hu-B1.219 have been identified, and they differ in sequence only at their 3' ends. The sequences are expressed in certain human fetal and tumor cells. Therefore, a wide variety of uses are encompassed by the present invention, including but not limited to, the diagnosis of cancer, the marking of fetal tissues, and the screening of ligands and compounds that bind the receptor molecule encoded by Hu-B1.219.

For the purpose of the present invention, the designation Hu-B1.219 refers to the complete cDNA sequence disclosed in FIGS. 2A–2E. In addition, Hu-B1.219 also refers to the partial coding sequences within the cDNA sequence of FIGS. 2A–2E.

4. BRIEF DESCRIPTION OF THE DRAWINGS

FIG. 1. A schematic drawing of conserved regions shared by members of HR family.

FIGS. 2A–2G. Nucleotide sequence (SEQ ID NO: 6) and deduced amino acid sequence (SEQ ID NOS: 7, 8, 9) of Hu-B1.219.

FIG. 3A. Comparison of 3' end nucleotide sequences of the three forms of the Hu-B1.219 Form 1 (SEQ ID NO:10); Form 2 (SEQ ID NO:13); Form 3 (SEQ ID NO:16).

FIG. 3B. Comparison of 3' end amino acid sequences of the three forms of Hu-B1.219 Form 1 (SEQ ID NOS:11, 12); Form 2 (SEQ ID NOS:14, 15); Form 3 (SEQ ID NOS:17, 18, 19). The * symbol indicates a stop codon.

FIG. 4. Comparison of the spacing of conserved amino acids in the FN III domain between HR genes and Hu-B1.219.

FIG. 5. Comparison of conserved motifs between HR molecules and Hu-B1.219 in "Block 3" mIL2Rβ (SEQ ID NO:20); hIL2Rγ (SEQ ID NO:21); mIL5Rα (SEQ ID NO:22); mEPOR (SEQ ID NO:23); Hu-B1.219(5') (SEQ ID NO:24); Hu-B1.219(3') (SEQ ID NO:25).

FIG. 6. Comparison of conserved motifs between HR molecules and Hu-B1.219 in "Block 6" mIL-2Rβ (SEQ ID NO:26); hIL-2Rγ (SEQ ID NO:27); mIL-5Rα (SEQ ID NO:28); mEPOR (SEQ ID NO:29); Hu-B1.219(5') (SEQ ID NO:30); Hu-B1.219(3') (SEQ ID NO:31).

5. DETAILED DESCRIPTION OF THE INVENTION

5.1. THE Hu-B1.219 CODING SEQUENCE

The present invention relates to nucleic acid and amino acid sequences of a novel member of the HR family. In a specific embodiment by way of example in Section 6, infra, a new member of this HR family of receptors was cloned and characterized. The nucleotide coding sequence and deduced amino acid sequence of the novel receptor are unique, and the receptor is referred to as Hu-B1.219. In accordance with the invention, any nucleotide sequence which encodes the amino acid sequence of the Hu-B1.219 gene product can be used to generate recombinant molecules which direct the expression of Hu-B1.219 gene.

Analysis of the Hu-B1.219 sequence revealed significant homology to the FN III domain of the HR family indicating that it was a member of the HR family of receptors. The shared homology between Hu-B1.219 and other known members of the HR family is discussed in Section 6.2, infra. However, this receptor also contains regions of previously unreported unique nucleotide sequences.

Northern blot hybridization analysis, indicates that Hu-B1.219 mRNA is highly expressed in cells of hematopoietic origin. In addition, the Hu-B1.219 sequence is expressed in certain tumor cells.

In order to clone the full length cDNA sequence encoding the entire Hu-B1.219 cDNA or to clone variant forms of the molecule, labeled DNA probes made from nucleic acid fragments corresponding to any portion of the partial cDNA disclosed herein may be used to screen the human fetal liver cDNA library. More specifically, oligonucleotides corresponding to either the 5' or 3' terminus of the partial cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabeled probe is then denatured by heating to 95° C. for 2 minutes and then added to the prehybridization solution containing the filters. The filters are hybridized at 60° C. for 16 hours. The filters are then washed in 1×wash mix (10×wash mix contains 3M NaCl, 0.6M Tris base, and 0.02M EDTA) twice for 5 minutes each at room temperature, then in 1×wash mix containing 1% SDS at 60° C. for 30 minutes, and finally in 0.3×wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready cDNA synthesized from human fetal liver containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and transmembrane domain, and finally overall structural similarity to known HR genes.

5.2. EXPRESSION OF Hu-B1.219 SEQUENCE

In accordance with the invention, Hu-B1.219 polynucleotide sequence which encodes the Hu-B1.219 protein, peptide fragments of Hu-B1.219, Hu-B1.219 fusion proteins. or functional equivalents thereof, may be used to generate recombinant DNA molecules that direct the expression of Hu-B1.219 protein, Hu-B1.219 peptide fragment, fusion proteins or a-functional equivalent thereof, in appropriate host cells. Such Hu-B1.219 polynucleotide sequences, as well as other polynucleotides which selectively hybridize to at least a part of such Hu-B1.219 polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Hu-B1.219 protein. Such DNA sequences include those which are capable of hybridizing to the human Hu-B1.219 sequences under stringent conditions. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1 % bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium citrate), 5×Denhardt's solution, sonicated salmon sperm DNA (50 µg/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Hu-B1.219 sequence, which result in a silent change thus producing a functionally equivalent Hu-B1.219 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively,charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter an Hu-B1.219 coding sequence for a variety of ends including but not limited to alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, an Hu-B1.219 or a modified Hu-B1.219 sequence may be ligated to a heterologous sequence to encode a fusion protein. For example, for screening of peptide libraries for inhibitors or stimulators of Hu-B1.219 activity, it may be useful to encode a chimeric Hu-B1.219 protein expressing a heterologous epitope that is recognized by a commercially available antibody. A fusion protein may also be engineered to contain a cleavage site located between a Hu-B1.219 sequence and the heterologous protein sequence, so that the Hu-B1.219 may be cleaved away from the heterologous moiety.

In an alternate embodiment of the invention, the coding sequence of a Hu-B1.219 could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10) :2331; Matteucci and Caruthers, 1980, *Tetrahedron Letters* 21:719; and Chow and Kempe, 1981, *Nuc. Acids Res.* 9(12):2807-2817. Alternatively, the protein itself could be produced using chemical methods to synthesize an Hu-B1.219 amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles,* W. H. Freeman and Co., N.Y., pp. 34–49).

In order to express a biologically active Hu-B1.219, the nucleotide sequence coding for Hu-B1.219, or a functional equivalent, is inserted into an appropriate expression vector, i.e., a vector which contains the necessary elements for the transcription and translation of the inserted coding sequence. The Hu-B1.219 gene products as well as host cells or cell lines transfected or transformed with recombinant Hu-B1.219 expression vectors can be used for a variety of purposes. These include but are not limited to generating antibodies (i.e., monoclonal or polyclonal) that competitively inhibit activity of an Hu-B1.219 and neutralize its activity; and antibodies that mimic the activity of Hu-B1.219 ligands in stimulating the receptor to transmit an intracellular signal. Anti-Hu-B1.219 antibodies may be used in detecting and quantifying expression of Hu-B1.219 levels in cells and tissues.

5.3. EXPRESSION SYSTEMS

Methods which are well known to those skilled in the art can be used to construct expression vectors containing the Hu-B1.219 coding sequence and appropriate transcriptional/ translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the Hu-B1.219 coding sequence. These include but are not limited to microorganisms such as bacteria transformed with recombinant bacteriophage DNA, plasmid DNA or cosmid DNA expression vectors containing the Hu-B1.219 coding sequence; yeast transformed with recombinant yeast expression vectors containing the Hu-B1.219 coding sequence; insect cell systems infected with recombinant virus expression vectors (e.g., baculovirus) containing the Hu-B1.219 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Hu-B1.219 coding sequence; or animal cell systems The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Hu-B1.219 DNA, SV40-, BPV- and EBV-based vectors may be used with an appropriate selectable marker.

In bacterial systems a number of expression vectors may be advantageously selected depending upon the use intended for the Hu-B1.219 expressed. For example, when large quantities of Hu-B1.219 are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., 1983, EMBO J. 2:1791), in which the Hu-B1.219 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the Hu-B1.219 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.c., soybean hsp17.5-E or hsp17.3-B (Gurley et al., 1986, Mol. Cell. Biol. 6:559–565) may be used. These constructs can be introduced into plant.. cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express Hu-B1.219 is an insect system. In one such system, Autographa californica nuclear polyhidrosis virus (AcNPV) is used as a vector to express foreign genes. The virus grows in Spodoptera frugiperda cells. The Hu-B1.219 coding sequence may be cloned into non-essential regions (for example the polyhedrin gene) of the virus and placed under control of an AcNPV promoter (for example the polyhedrin promoter). Successful insertion of the Hu-B1.219 coding sequence will result in inactivation of the polyhedron gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith et al., 1983, J. Virol. 46:584; Smith, U.S. Pat. No. 4,215,051).

In mammalian host cells, a number of viral based expression systems may be utilized. In cases where an adenovirus is used as an expression vector, the Hu-B1.219 coding sequence may be ligated to an adenovirus transcription/ translation control complex, e.g., the late promoter and tripartite leader sequence. This chimeric gene may then be inserted in the adenovirus genome by in vitro or in vivo recombination. Insertion in a non-essential region of the viral genome (e.c., region E1 or E3) will result in a recombinant virus that is viable and capable of expressing Hu-B1.219 in infected hosts. (e.g., See Logan & Shenk, 1984, Proc. Natl. Acad. Sci. USA 81:3655–3659). Alternatively, the vaccinia 7.5K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Specific initiation signals may also be required for efficient translation of inserted Hu-B1.219 coding sequences. These signals include the ATG initiation codon and adjacent sequences. In cases where the entire Hu-B1.219 gene, including its own initiation codon and adjacent sequences, is inserted into the appropriate expression vector, no additional translational control signals may be needed. However, in cases where only a portion of the Hu-B1.219 coding sequence is inserted, exogenous translational control signals, including the ATG initiation codon, must be provided. Furthermore, the initiation codon must be in phase with the reading frame of the Hu-B1.219 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.c., cleavage) of protein products may be important for the function of the protein. The presence of several consensus N-glycosylation sites in the Hu-B1.219 extracellular domain support the possibility that proper modification may be important for Hu-B1.219 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the Hu-B1.219 may be engineered. Rather than using expression vectors which contain viral origins of replication, host cells can be transformed with the Hu-B1.219 DNA controlled by appropriate expression control elements (e., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Hu-B1.219 on the cell surface. Such engineered cell lines are particularly useful in screening for ligands or drugs that affect Hu-B1.219 function.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk−, hgprt− or aprt− cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.4. IDENTIFICATION OF CELLS THAT EXPRESS Hu-B1.219

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of Hu-B1.219 mRNA transcripts in the host cell; and (d) detection of the gene product as measured by immunoassay or by its biological activity. Prior to the identification of gene expression, the host cells may be first mutagenized in an effort to increase the level of expression of Hu-B1.219, especially in cell lines that produce low amounts of Hu-B1.219.

In the first approach, the presence of the Hu-B1.219 coding sequence inserted in the expression vector can be detected by DNA-DNA or DNA-RNA hybridization using probes comprising nucleotide sequences that are homologous to the Hu-B1.219 coding sequence, respectively, or portions or derivatives thereof.

In the second approach, the recombinant expression vector/host system can be identified and selected based upon the presence or absence of certain "marker" gene functions (e.g. thymidine kinase activity, resistance to antibiotics, resistance to methotrexate, transformation phenotype, occlusion body formation in baculovirus, etc.). For example, if the Hu-B1.219 coding sequence is inserted within a marker gene sequence of the vector, recombinants containing the Hu-B1.219 coding sequence can be identified by the absence of the marker gene function. Alternatively, a marker gene can be placed in tandem with the Hu-B1.219 sequence under the control of the same or different promoter used to control the expression of the Hu-B1.219 coding sequence. Expression of the marker in response to induction or selection indicates expression of the Hu-B1.219 coding sequence.

In the third approach, transcriptional activity for the Hu-B1.219 coding region can be assessed by hybridization assays. For example, RNA can be isolated and analyzed by Northern blot using a probe homologous to the Hu-B1.219 coding sequence or particular portions thereof. Alternatively, total nucleic acids of the host cell may be extracted and assayed for hybridization to such probes.

In the fourth approach, the expression of the Hu-B1.219 protein product can be assessed immunologically, for example by Western blots, immunoassays such as radioimmuno-precipitation, enzyme-linked immunoassays and the like.

5.5. USES OF Hu-B1.219 ENGINEERED CELL LINES

In an embodiment of the invention, the Hu-B1.219 receptor and/or cell lines that express the Hu-B1.219 receptor may be used to screen for antibodies, peptides, or other ligands that act as agonists or antagonists of the Hu-B1.219 receptor. For example, anti-Hu-B1.219 antibodies may be used to inhibit or stimulate receptor Hu-B1.219 function. Alternatively, screening of peptide libraries with recombinantly expressed soluble Hu-B1.219 protein or cell lines expressing Hu-B1.219 protein may be useful for identification of therapeutic molecules that function by inhibiting or stimulating the biological activity of Hu-B1.219. The uses of the Hu-B1.219 receptor and engineered cell lines, described in the subsections below, may be employed equally well for other members of the HR family.

In an embodiment of the invention, engineered cell lines which express most of the Hu-B1.219 coding region or its ligand binding domain or its ligand binding domain fused to another molecule such as the immunoglobulin constant region (Hollenbaugh and Aruffo, 1992, Current Protocols in Immunology, Unit 10.19; Aruffo et al., 1990, Cell 61:1303) may be utilized to produce a soluble receptor to screen and identify ligand antagonists as well as agonists. The soluble Hu-B1.219 protein or fusion protein may be used to identify a ligand in binding assays, affinity chromatography, immunoprecipitation, Western blot, and the like. Alternatively, the ligand binding domain of Hu-B1.219 may be fused to the coding sequence of the epidermal growth factor receptor transmembrane and cytoplasmic regions. This approach provides for the use of the epidermal growth factor receptor signal transduction pathway as a means for detecting ligands that bind to Hu-B1.219 in a manner capable of triggering an intracellular signal. Synthetic compounds, natural products, and other sources of potentially biologically active materials can be screened in a number of ways.

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that stimulate or inhibit the biological activity of receptors through their interactions with the given receptor.

Identification of molecules that are able to bind to the Hu-B1.219 may be accomplished by screening a peptide library with recombinant soluble Hu-B1.219 protein. Methods for expression and purification of Hu-B1.219 are described in Section 5.2, supra, and may be used to express recombinant full length Hu-B1.219 or fragments of Hu-B1.219 depending on the functional domains of interest. For example, the cytoplasmic and extracellular ligand binding domains of Hu-B1.219 may be separately expressed and used to screen peptide libraries.

To identify and isolate the peptide/solid phase support that interacts and forms a complex with Hu-B1.219, it is necessary to label or "tag" the Hu-B1.219 molecule. The Hu-B1.219 protein may be conjugated to enzymes such as. alkaline phosphatase or horseradish peroxidase or to other reagents such as fluorescent labels which may include fluorescein isothiocyanate (FITC), phycoerythrin (PE) or rhodamine. Conjugation of any given label to Hu-B1.219 may be performed using techniques that are routine in the art. Alternatively, Hu-B1.219 expression vectors may be engineered to express a chimeric Hu-B1.219 protein containing an epitope for which a commercially available antibody exist. The epitope specific antibody may be tagged using methods well known in the art including labeling with enzymes, fluorescent dyes or colored or magnetic beads.

The "tagged" Hu-B1.219 conjugate is incubated with the random peptide library for 30 minutes to one hour at 22° C. to allow complex formation between Hu-B1.219 and peptide species within the library. The library is then washed to remove any unbound Hu-B1.219 protein. If Hu-B1.219 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4'-diaminobenzidine (DAB), respectively. After incubating for several minutes, the peptide/solid phase-Hu-B1.219 complex changes color, and can be easily identified and isolated physically under a dissecting microscope with a micromanipulator. If a fluorescent tagged Hu-B1.219 molecule has been used, complexes may be isolated by fluorescent activated sorting. If a chimeric Hu-B1.219 protein expressing a heterologous epitope has been used, detection of the peptide/Hu-B1.219 complex may be accomplished by using a labeled epitope specific antibody. Once isolated, the identity of the peptide attached to the solid phase support may be determined by peptide sequencing.

In addition to using soluble Hu-B1.219 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing Hu-B1.219 are described in Section 5.3. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

Various procedures known in the art may be used for the production of antibodies to epitopes of the recombinantly produced Hu-B1.219 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind Hu-B1.219 may be radioactively labeled allowing one to follow their location and distribution in the body after injection. Radioisotope tagged antibodies may be used as a non-invasive diagnostic tool for imaging de novo cells of tumors and metastases.

Immunotoxins may also be designed which target cytotoxic agents to specific sites in the body. For example, high affinity Hu-B1.219 specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Hu-B1.219 expressing tumor cells.

For the production of antibodies, various host animals may be immunized by injection with the Hu-B1.219 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to Hu-B1.219 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce Hu-B1.219-specific single chain antibodies.

Antibody fragments which contain specific binding sites of Hu-B1.219 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Hu-B1.219.

5.6. USES OF Hu-B1.219 POLYNUCLEOTIDE

An Hu-B1.219 polynucleotide may be used for diagnostic and/or therapeutic purposes. For diagnostic purposes, an Hu-B1.219 polynucleotide may be used to detect Hu-B1.219 gene expression or aberrant Hu-B1.219 gene expression in disease states, e.g., chronic myelogenous leukemia. Included in the scope of the invention are oligonucleotide sequences, that include antisense RNA and DNA molecules and ribozymes, that function to inhibit translation of an Hu-B1.219.

5.6.1. DIAGNOSTIC USES OF AN Hu-B1.219 POLYNUCLEOTIDE

An Hu-B1.219 polynucleotide may have a number of uses for the diagnosis of diseases resulting from aberrant expression of Hu-B1.219. For example, the Hu-B1.219 DNA sequence may be used in hybridization assays of biopsies or autopsies to diagnose abnormalities of Hu-B1.219 expression; e.g., Southern or Northern analysis, including in situ hybridization assays. Such techniques are well known in the art, and are in fact the basis of many commercially available diagnostic kits.

5.6.2. THERAPEUTIC USES OF AN Hu-B1.219 POLYNUCLEOTIDE

An Hu-B1.219 polynucleotide may be useful in the treatment of various abnormal conditions. By introducing gene sequences into cells, gene therapy can be used to treat conditions in which the cells do not proliferate or differentiate normally due to underexpression of normal Hu-B1.219 or expression of abnormal/inactive Hu-B1.219. In some instances, the polynucleotide encoding an Hu-B1.219 is intended to replace or act in the place of a functionally deficient endogenous gene. Alternatively, abnormal conditions characterized by overproliferation can be treated using the gene therapy techniques described below.

Abnormal cellular proliferation is an important component of a variety of disease states. Recombinant gene therapy vectors, such as viral vectors, may be engineered to express variant, signalling incompetent forms of Hu-B1.219 which may be used to inhibit the activity of the naturally occurring endogenous Hu-B1.219. A signalling incompetent form may be, for example, a truncated form of the protein that is lacking all or part of its signal transduction domain. Such a truncated form may participate in normal binding to a substrate but lack signal transduction activity. Thus recombinant gene therapy vectors may be used therapeutically for treatment of diseases resulting from aberrant expression or activity of an Hu-B1.219. Accordingly, the invention provides a method of inhibiting the effects of signal transduction by an endogenous Hu-B1.219 protein in a cell comprising delivering a DNA molecule encoding a signalling incompetent form of the Hu-B1.219 protein to the cell so that the signalling incompetent Hu-B1.219 protein is produced in the cell and competes with the endogenous Hu-B1.219 protein for access to molecules in the Hu-B1.219 protein signalling pathway which activate or are activated by the endogenous Hu-B1.219 protein.

Expression vectors derived from viruses such as retroviruses, vaccinia virus, adeno-associated virus, herpes viruses, or bovine papilloma virus, may be used for delivery of recombinant Hu-B1.219 into the targeted cell population. Methods which are well known to those skilled in the art can be used to construct recombinant viral vectors containing an Hu-B1.219 polynucleotide sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant Hu-B1.219 molecules can be reconstituted into liposomes for delivery to target cells.

Oligonucleotide sequences, that include anti-sense RNA and DNA molecules and ribozymes that function to inhibit the translation of an Hu-B1.219 mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an Hu-B1.219 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of Hu-B1.219 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2'O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of an Hu-B1.219 polynucleotide in a cell ex vivo, i.e., for use in autologous cell therapy, the use of a vector such as a virus, retrovirus, phage or plasmid, etc. or techniques such as electroporation which may be used in vivo or ex vivo.

6. EXAMPLE

Molecular Cloning of a Novel Hematopoietin Receptor Complementary DNA

6.1. MATERIALS AND METHODS

6.1.1. NORTHERN BLOT ANALYSIS

In order to study the expression of the Hu-B1.219 gene, Northern blots containing RNA obtained from a variety of human tissues (Clontech, Palo Alto, Calif.) were hybridized with a radiolabeled 530 base pair (bp) DNA probe corresponding to nucleotides #578 through 1107 (see FIGS. 2A–2E). Briefly, the blots were prehybridized at 42° C. for 3–6 hours in a solution containing 5×SSPE, 10×Denhardt's solution, 100 µg/ml freshly denatured, sheared salmon sperm DNA, 50% formamide (freshly deionized), and 2% SDS. The radiolabeled probe was heat denatured and added to the prehybridization mix and allowed to hybridize at 42° C. for 18–24 hours with constant shaking. The blots were rinsed in 2×SSC, 0.05% SDS several times at room temperature before being transferred to a wash solution containing 0.1×SSC, 0.1% SDS and agitated at 50° C. for 40 minutes. The blots were then covered with plastic wrap, mounted on Whatman paper and exposed to x-ray film at −70° C. using an intensifying screen.

6.1.2. REVERSE TRANSCRIPTION/POLYMERASE CHAIN REACTION (RT/PCR)

Total RNA was isolated using standard laboratory procedures (Sambrook et al., 1989, Molecular Cloning, A Laboratory Manual, Cold Spring Harbor Laboratory, NY). Approximately 1 µg of total RNA was reverse transcribed and the cDNA was amplified by PCR (Perkin Elmer, Norwalk, Conn.). The PCR amplification conditions were the same for Hu-B1.219 and Form 1 expression analysis. They were: 94° C. for 30 sec, 60° C. for 30 sec, 72° C. for 30 sec for a total of 40 cycles. The amplified products (224 bp for Hu-B1.219 and 816 bp for Form 1) were resolved by agarose gel electrophoresis and visualized by ethidium bromide staining. The Hu-B1.219 amplimers were GGTTTG-CATATGGAAGTC (SEQ ID NO:2) (upper) and CCT-GAACCATCCAGTCTCT (SEQ ID NO:3) (lower). The Form 1 specific amplimers were GACTCATTGTGCAGT-GTTCAG (SEQ ID NO:4) (upper) and TAGTGGAGG-GAGGGTCAGCAG (SEQ ID NO:5) (lower). The upper amplimer was commonly shared by all 3 forms, whereas the lower amplimer was Form 1-specific.

6.2. RESULTS

A number of cDNA clones were isolated from a human fetal liver cDNA library (Clontech, Palo Alto, Calif.), and the DNA sequences of several of these clones were determined. These clones (Hu-B1.219 #4, #33, #34, #1, #36, #8, #55, #60, #3, #57, #62) contained overlapping sequences, which were then compiled into a contiguous nucleotide sequence. Both the cDNA sequence and predicted protein sequence from the cDNA are shown in FIGS. 2A–2E. This cDNA sequence contains two FN III domains, each containing a "WS box", which are characteristic of genes of the HR family. However, the Hu-B1.219 sequence is not identical to any known gene. Thus, this cDNA represents a novel member of the HR gene family, herein referred to as Hu-B1.219 (Table 1).

TABLE 1

| Cytokine Receptor Gene FN III Domain Sizes (bp) | | | |
| --- | --- | --- | --- |
| Gene | Human | Mouse | Rat |
| Hu-B1.219(5') | 273 | | |
| Hu-B1.219(3') | 282 | | |
| IL-2Rβ | 291 | 288 | 291 |
| IL-2Rγ | 273 | | |
| IL-3Rα | 246 | 252 | |
| IL-3RβAic2a | | 306 and 273 | |
| IL-3RβAic2b | 306 and 282 | 303 and 276 | |
| IL-4R | 294 | | 291 |
| IL-5Rα | 276 | 273 | |
| IL-6R | 288 | 285 | |
| gp130 | 288 | 291 | 288 |
| IL-7R | | 294 | |
| IL-9R | 321 | 321 | |
| mpl | | 270 | |
| G-CSFR | 300 | 297 | |
| GM-CSFR | 288 | | |
| CNTFR | 282 | | 285 |
| PRLR | | | 288 |
| EPOR | 288 | 285 | 288 |
| LIFR-1 | 321 and 297 | | |

Based on the sequence of Hu-B1.219 presented in FIGS. 2A–2E, the translation initiation site appears at position #97. The sequence encodes an open reading frame up to and including nucleotide #2970. It is believed that the sequence between nucleotides #2614 and #2691 encodes a transmembrane domain. The complete sequence encodes a protein of 958 amino acids.

However, the sequence in FIGS. 2A–2E represents only one form of Hu-B1.219 cDNA sequence, herein referred to as Form 1. This is because additional lambda clones were discovered that contained different sequences near the 3' end known as Form 2 and Form 3. All three forms contain the identical sequence up to an d including nucleotide #2770, then they diverge at nucleotide #2771 and beyond (FIG. 3A). An alignment of deduced amino acid sequences of all three forms corresponding to the 3' end from #2771 until a stop codon is shown in FIG. 3B. Two of the originally isolated lambda clones, #36 and #8, contain the 3' end sequences of Form 1 and Form 2, respectively. These three forms of Hu-B1.219 may derive from a common precursor mRNA by an alternative splicing mechanism.

It is noteworthy that the DNA sequence of Form 1 from nucleotide #2771 to the end is 98% identical to a human retrotransposon sequence that is thought to be derived from a human endogenous retroviral DNA sequence (Singer, 1982, Cell 28:433; Weiner et al., 1986, Ann. Rev. Biochem. 55:631; Lower et al., 1993, Proc. Natl. Acad. Sci. USA 90:4480). In order to examine the expression of the different forms of cDNA, RT/PCR was performed using several human cell lines. The results in Table 2 show that Form 1 was expressed as RNA in K-562 cells and in a human fetal liver cDNA preparation. Since Hu-B1.219 was cloned from human fetal liver cDNA library, this served as a positive control. However, with respect to several other human cell lines, Form 1 was not detected, whereas Hu-B1.219 expression was positive. For example, Form 1 was not expressed in KG1a cells, but Form 3 was expressed. Thus, it is possible that these three forms of Hu-B1.219 are not expressed simultaneously in the same cells. There may be selective expression of certain forms in particular cell populations.

TABLE 2

RT/PCR Analysis of Hu-B1.219 Expression

| Cell Lines | Hu-B1.219* | Form 1Δ | Form 3Δ |
| --- | --- | --- | --- |
| MRC5 (Lung fibroblast) | ++ | +/− | + |
| KG1a (lymphoblast) | + | − | ++ |
| Raji (B cell lymphoma) | + | − | + |
| Kit 225/K6 (T cell) | +++ | − | + |
| K562 (myelogenous leukemia) | ++++ | +++ | ++++ |
| Human Fetal Liver (positive control) | +++ | +++ | +++ |

*Analysis by Northern blots
ΔAnalysis by RT/PCR

Various human tissue RNA were probed with a radiolabelled Hu-B1.219 fragment corresponding to nucleotide numbers from #578 to #1107 as disclosed in FIGS. 2A–2E for Northern blot analyses. Two different size mRNAs were detected. This result suggests that there may be another homologous gene or there is alternative splicing of a single RNA transcript. Hu-B1.219 expression was by far the strongest in human fetal tissues, particularly the liver and lung. Trace levels were found in several adult tissues. Interestingly, a chronic myelogenous leukemia cell line, K562, was strongly positive for its expression, while some expression was also detected in A549 cells, a lung carcinoma cell line (Table 3).

TABLE 3

SUMMARY OF NORTHERN BLOT ANALYSIS OF Hu-B1.219 GENE EXPRESSION

| Human Tissues/cell lines | Expression |
| --- | --- |
| fetal brain | − |
| lung | +++ |
| liver | +++++ |
| kidney | + |

TABLE 3-continued

SUMMARY OF NORTHERN BLOT ANALYSIS OF Hu-B1.219 GENE EXPRESSION

| Human Tissues/cell lines | Expression |
| --- | --- |
| adult heart | + |
| brain | − |
| placenta | +/− |
| lung | + |
| liver | + |
| skeletal muscle | − |
| kidney | +/− |
| pancreas | − |
| spleen | − |
| thymus | − |
| prostate | − |
| testis | − |
| ovary | + |
| small intestine | − |
| colon | − |
| peripheral blood leukocytes | − |
| cancer HL-60 | − |
| HeLa | − |
| K-562 | +++ |
| MOLT-4 | − |
| Raji | − |
| SW480 | − |
| A549 | + |
| G361 | − |

Taken together, the data indicates that the Hu-B1.219 cDNA clone represents a new member of the human hematopoietin receptor family. A summary of the data that supports this conclusion is as follows:

1. The Hu-B1.219 DNA and protein sequences do not fully match any known sequences in the corresponding computer data bases.
2. Hu-B1.219 shares certain DNA sequence homology with the IL-6R and IL-4R.
3. It shares certain protein homology with G-CSFR, IL-6R, IL-3R beta chain, gp130, IL-12R, and LIFR.
4. It contains two "WS box" motifs with the correct spacing of conserved amino acids in the FN III domains (see FIG. 4).
5. It contains an amphipathic sequence in block 3 of the FN III domains (see FIG. 5).
6. It contains alternating hydrophobic and basic amino acids in block 6 of the FN III domains (see FIG. 6).
7. It contains conserved cysteines in these cysteine rich regions upstream of the FN III domains.
8. It was originally cloned from a hematopoietic tissue, fetal liver.
9. It is expressed by certain fetal tissues.

7. Deposit of Microorganisms

The following organisms were deposited with the American Type Culture Collection (ATCC), 12301 Parklawn Drive, Rockville, Md. 20852.

| Strain Designation | Accession No. |
| --- | --- |
| HuB1.219, #1 | 75885 |
| HuB1.219, #4 | 75886 |

| Strain Designation | Accession No. |
|---|---|
| HuB1.219, #8 | 75887 |
| HuB1.219, #33 | 75888 |
| HuB1.219, #34 | 75889 |
| HuB1.219, #36 | 75890 |
| HuB1.219, #55 | |
| HuB1.219, #60 | |
| HuB1.219, #3 | |
| HuB1.219, #57 | |
| HuB1.219, #62 | |

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of identifying a compound that binds to an Hu-B1.219 receptor, comprising the steps of:
    (a) contacting an Hu-B1.219 receptor, an Hu-B1.219 receptor ligand binding domain or a fusion protein comprising an Hu-B1.219 receptor ligand binding domain with a compound;
    (b) determining whether the compound binds to the Hu-B1.219 receptor, the Hu-B1.219 receptor ligand binding domain or the fusion protein; and
    (c) determining the identity of the bound compound.

2. The method of claim 1 in which in step (a), the compound is contacted with an Hu-B1.219 receptor.

3. The method of claim 2 in which the receptor comprises an amino acid sequence corresponding to residues # 3 to # 893 of SEQ ID NO:8.

4. The method of claim 2 in which the receptor comprises an amino acid sequence corresponding to residues # 3 to # 960 of SEQ ID NO:8.

5. The method of claim 2 in which the receptor comprises an amino acid sequence corresponding to SEQ ID NO:32.

6. The method of claim 2 in which the receptor comprises an amino acid sequence corresponding to SEQ ID NO:33.

7. The method of claim 2 in which the receptor is soluble.

8. The method of claim 7 in which the soluble receptor comprises an amino acid sequence corresponding to residues # 3 to # 841 of SEQ ID NO:8.

9. The method of claim 2 in which the receptor is associated with a membrane of an intact cell.

10. The method of claim 9 in which the intact cell expresses a polynucleotide encoding the Hu-B1.219 receptor.

11. The method of claim 10 in which the polynucleotide comprises a nucleotide sequence selected from the group consisting of:
    (a) a nucleotide sequence corresponding to nucleotides # 97 to # 2770 of SEQ ID NO:6;
    (b) a nucleotide sequence which is complementary to (a); or
    (c) a nucleotide sequence that hybridizes under stringent conditions to (a) or (b), wherein the stringent conditions are selected from the group consisting of:
        (i) washing at 50° C. with 0.015 M NaCl, 0.0015 M sodium citrate and 0.1% SDS;
        (ii) hybridization at 42° C. with 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate; and
        (iii) hybridization at 42° C. with 50% (vol/vol) formamide with 5×SSC, 5×Denhardt's solution, 50 µg/ml salmon sperm DNA, 0.1% SDS, and 10% dextran sulfate, with washes at 42° C. in 0.2×SSC and 0.1% SDS.

12. The method of claim 11 in which the polynucleotide comprises (a) or (b).

13. The method of claim 11 or 12 in which the nucleotide sequence of (a) further includes at its 3'-end a nucleotide sequence corresponding to nucleotides # 2771 to # 2970 of SEQ ID NO:6.

14. The method of claim 11 or 12 in which the nucleotide sequence of (a) further includes at its 3'-end a nucleotide sequence corresponding to nucleotides # 2771 to # 2991 of SEQ ID NO:6.

15. The method of claim 11 or 12 in which the nucleotide sequence of (a) further includes at its 3'-end a nucleotide sequence corresponding to nucleotides # 21 to # 64 of SEQ ID NO:13.

16. The method of claim 11 or 12 in which the nucleotide sequence of (a) further includes at its 3'-end a nucleotide sequence corresponding to nucleotides # 21 to # 130 of SEQ ID NO:13.

17. The method of claim 11 or 12 in which the nucleotide sequence of (a) further includes at its 3'-end a nucleotide sequence corresponding to nucleotides # 21 to # 34 of SEQ ID NO:16.

18. The method of claim 11 or 12 in which the nucleotide sequence of (a) further includes at its 3'-end a nucleotide sequence corresponding to nucleotides # 21 to # 100 of SEQ ID NO:16.

19. The method of claim 11 or 12 in which the nucleotide sequence of (a) further includes at its 3'-end a nucleotide sequence corresponding to nucleotides # 21 to # 118 of SEQ ID NO:16.

20. The method of claim 11 or 12 in which the nucleotide sequence of (a) further includes at its 3'-end a nucleotide sequence corresponding to nucleotides # 21 to # 127 of SEQ ID NO:16.

21. The method of claim 2 in which the receptor is associated with a liposome.

22. The method of claim 1 in which in step (a), the compound is contacted with all Hu-B1.219 receptor ligand binding domain.

23. The method of claim 1 in which in step (a), the compound is contacted with a fusion protein comprising an Hu-B1.219 receptor ligand binding domain.

24. The method of claim 23 in which the Hu-B1.219 receptor ligand binding domain is fused to a constant region of an immunoglobulin.

25. The method of claim 23 in which the Hu-B1.219 receptor ligand binding domain is fused to an epidermal growth factor receptor transmembrane and cytoplasmic domain.

26. The method of claim 23 in which the ligand binding domain comprises an amino acid sequence corresponding to residues # 3 to # 841 of SEQ ID NO:8.

27. The method of claim 23 in which the fusion protein is associated with a membrane of an intact cell.

28. The method of claim 27 in which the intact cell expresses a polynucleotide encoding the fusion protein.

29. The method of claim 28 in which the polynucleotide comprises a nucleotide sequence corresponding to nucleotides # 97 to # 2613 of SEQ ID NO:6.

30. The method of claim 29 in which the nucleotide sequence further includes at its 3'-end a nucleotide sequence that encodes epidermal growth factor receptor transmembrane and cytoplasmic membrane domains.

31. The method of claim 1 in which the Hu-B1.219 receptor, the Hu-B1.219 receptor ligand binding domain or the fusion protein is labeled.

32. The method of claim 31 in which the label is selected from the group consisting of an enzyme, a fluorophore or an epitope of an antibody.

33. The method of claim 1 in which the compound is bound to a solid support.

34. A method of identifying a compound that binds to an Hu-B1.219 receptor, comprising the steps of:
(a) contacting a cell that expresses an Hu-B1.219 receptor or a fusion protein comprising an Hu-B1.219 receptor ligand binding domain with a compound;
(b) determining whether the compound binds the Hu-B1.219 receptor or fusion protein; and
(c) determining the identity of the bound compound.

35. The method of claim 34 in which the receptor comprises an amino acid sequence corresponding to residues # 3 to # 893 of SEQ ID NO:8.

36. The method of claim 34 in which the receptor comprises an amino acid sequence corresponding to residues # 3 to # 960 of SEQ ID NO:8.

37. The method of claim 34 in which the receptor comprises an amino acid sequence corresponding to SEQ ID NO:32.

38. The method of claim 34 in which the receptor comprises an amino acid sequence corresponding to SEQ ID NO:33.

39. The method of claim 34 in which the Hu-B1.219 receptor ligand binding domain comprises an amino acid sequence corresponding to residues # 3 to # 841 of SEQ ID NO:8.

40. The method of claim 39 in which the Hu-B1.219 receptor ligand binding domain is fused to an epidermal growth factor receptor transmembrane and cytoplasmic domain.

41. The method of claim 34 in which the cell is a cell that has been transfected with a polynucleotide encoding the Hu-B1.219 receptor, or progeny thereof.

42. The method of claim 41 in which the polynucleotide comprises a nucleotide sequence selected from the group consisting of:
(a) a nucleotide sequence corresponding to nucleotides # 97 to # 2770 of SEQ ID NO:6;
(b) a nucleotide sequence which is complementary to (a); or
(c) a nucleotide sequence that hybridizes under stringent conditions to (a) or (b) wherein the stringent conditions are selected from the group consisting of:
  (i) washing at 50° C. with 0.015 M NaCl, 0.0015 M sodium citrate and 0.1% SDS;
  (ii) hybridization at 42° C. with 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate; and
  (iii) hybridization at 42° C. with 50% (vol/vol) formamide with 5×SSC, 5×Denhardt's solution, 50 µg/ml salmon sperm DNA, 0.1% SDS, and 10% dextran sulfates with washes at 42° C. in 0.2×SSC and 0.1% SDS.

43. The method of claim 42 in which the polynucleotide comprises (a) or (b).

44. The method of claim 42 or 43 in which the nucleotide sequence of (a) further includes at its 3'-end a nucleotide sequence corresponding to nucleotides # 2771 to # 2970 of SEQ ID NO:6.

45. The method of claim 42 or 43 in which the nucleotide sequence of (a) further includes at its 3'-end a nucleotide sequence corresponding to nucleotides # 2771 to # 2991 of SEQ ID NO:6.

46. The method of claim 42 or 43 in which the nucleotide sequence of (a) further includes at its 3'-end a nucleotide sequence corresponding to nucleotides # 21 to # 64 of SEQ ID NO:13.

47. The method of claim 42 or 43 in which the nucleotide sequence of (a) further includes at its 3'-end a nucleotide sequence corresponding to nucleotides # 21 to # 130 of SEQ ID NO:13.

48. The method of claim 42 or 43 in which the nucleotide sequence of (a) further includes at its 3'-end a nucleotide sequence corresponding to nucleotides # 21 to # 34 of SEQ ID NO:16.

49. The method of claim 42 or 43 in which the nucleotide sequence of (a) further includes at its 3'-end a nucleotide sequence corresponding to nucleotides # 21 to # 100 of SEQ ID NO:16.

50. The method of claim 42 or 43 in which the nucleotide sequence of (a) further includes at its 3'-end a nucleotide sequence corresponding to nucleotides # 21 to # 118 of SEQ ID NO:16.

51. The method of claim 42 or 43 in which the nucleotide sequence of (a) further includes at its 3'-end a nucleotide sequence corresponding to nucleotides # 21 to # 127 of SEQ ID NO:16.

52. The method of claim 34 in which the cell is a cell that has been transfected with a polynucleotide encoding the fusion protein, or progeny thereof.

53. The method of claim 52 in which the polynucleotide comprises a nucleotide sequence corresponding to nucleotides #97 to #2613 of SEQ ID NO:6.

54. The method of claim 53 in which the nucleotide sequence further includes at its 3'-end a nucleotide sequence that encodes epidermal growth factor receptor transmembrane and cytoplasmic membrane domains.

55. The method of claim 34 in which the compound is bound to a solid support.

56. A method of identifying a compound that stimulates or inhibits a biological activity of an Hu-B1.219 receptor, comprising the steps of:
(a) contacting a cell that expresses an Hu-B1.219 receptor or a fusion protein comprising an Hu-B1.219 receptor ligand binding domain with a compound;
(b) determining whether the compound stimulates or inhibits a biological activity of the Hu-B1.219 receptor or fusion protein; and
(c) determining the identity of the stimulatory or inhibitory compound.

57. The method of claim 56 in which the receptor comprises an amino acid sequence corresponding to residues # 3 to # 893 of SEQ ID NO:8.

58. The method of claim 56 in which the receptor comprises an amino acid sequence corresponding to residues # 3 to # 960 of SEQ ID NO:8.

59. The method of claim 56 in which the receptor comprises an amino acid sequence corresponding to SEQ ID NO:32.

60. The method of claim 56 in which the receptor comprises an amino acid sequence corresponding to SEQ ID NO:33.

61. The method of claim 56 in which the Hu-B1.219 receptor ligand binding domain comprises an amino acid sequence corresponding to residues # 3 to # 841 of SEQ ID NO:8.

62. The method of claim 61 in which the Hu-B1.219 receptor ligand binding domain is fused to an epidermal growth factor receptor transmembrane and cytoplasmic domain.

63. The method of claim 56 in which the cell is a cell that has been transfected with a polynucleotide encoding the Hu-B1.219 receptor, or progeny thereof.

64. The method of claim 63 in which the polynucleotide comprises a nucleotide sequence selected from the group consisting of:
(a) a nucleotide sequence corresponding to nucleotides # 97 to # 2770 of SEQ ID NO:6;
(b) a nucleotide sequence which is complementary to (a); or
(c) a nucleotide sequence that hybridizes under stringent conditions to (a) or (b) wherein the stringent conditions are selected from the group consisting of:
(i) washing at 50° C. with 0.015 M NaCl, 0.0015 M sodium citrate and 0.1% SDS;
(ii) hybridization at 42° C. with 50% (vol/vol) formamide with 0.1% bovine serum albumin/0.1% Ficoll/ 0.1% polyvinylpyrrolidone/50 mM sodium phosphate buffer at pH 6.5 with 750 mM NaCl, 75 mM sodium citrate; and
(iii) hybridization at 42° C. with 50% (vol/vol) formamide with 5×SSC, 5×Denhardt's solution, 50 μg/ml salmon sperm DNA, 0.1% SDS, and 10% dextran sulfate, with washes at 42° C. in 0.2×SSC and 0.1% SDS.

65. The method of claim 64 in which the polynucleotide comprises (a) or (b).

66. The method of claim 64 or 65 in which the nucleotide sequence of (a) further includes at its 3'-end a nucleotide sequence corresponding to nucleotides # 2771 to # 2970 of SEQ ID NO:6.

67. The method of claim 64 or 65 in which the nucleotide sequence of (a) further includes at its 3'-end a nucleotide sequence corresponding to nucleotides # 2771 to # 2991 of SEQ ID NO:6.

68. The method of claim 64 or 65 in which the nucleotide sequence of (a) further includes at its 3'-end a nucleotide sequence corresponding to nucleotides # 21 to # 64 of SEQ ID NO:13.

69. The method of claim 64 or 65 in which the nucleotide sequence of (a) further includes at its 3'-end a nucleotide sequence corresponding to nucleotides # 21 to # 130 of SEQ ID NO:13.

70. The method of claim 64 or 65 in which the nucleotide sequence of (a) further includes at its 3'-end a nucleotide sequence corresponding to nucleotides # 21 to # 34 of SEQ ID NO:16.

71. The method of claim 64 or 65 in which the nucleotide sequence of (a) further includes at its 3'-end a nucleotide sequence corresponding to nucleotides # 21 to # 100 of SEQ ID NO:16.

72. The method of claim 64 or 65 in which the nucleotide sequence of (a) further includes at its 3'-end a nucleotide sequence corresponding to nucleotides # 21 to # 118 of SEQ ID NO:16.

73. The method of claim 64 or 65 in which the nucleotide sequence of (a) further includes at its 3'-end a nucleotide sequence corresponding to nucleotides # 21 to # 127 of SEQ ID NO:16.

74. The method of claim 56 in which the cell is a cell that has been transfected with a polynucleotide encoding the fusion protein, or progeny thereof.

75. The method of claim 74 in which the polynucleotide comprises a nucleotide sequence corresponding to nucleotides # 97 to # 2613 of SEQ ID NO:6.

76. The method of claim 75 in which the nucleotide sequence further includes at its 3'-end a nucleotide sequence that encodes epidermal growth factor receptor transmembrane and cytoplasmic membrane domains.

77. The method of claim 56 in which the compound is bound to a solid support.

* * * * *

UNITED STATES PATENT AND TRADEMARK OFFICE
CERTIFICATE OF CORRECTION

PATENT NO. : 6,524,806 B1  
DATED : February 25, 2003  
INVENTOR(S) : H. Ralph Snodgrass et al.

Page 1 of 1

It is certified that error appears in the above-identified patent and that said Letters Patent is hereby corrected as shown below:

<u>Title page,</u>  
Item [54], Title, change "HEMETOPOIETIN" to -- HEMATOPOIETIN --

<u>Column 2,</u>  
Line 8, change "Er." to -- Br. --.

<u>Column 8,</u>  
Line 59, change "(e.c.," to -- (e.g., --.

<u>Column 9,</u>  
Lines 23, 24 and 45, change "(e.c.," to -- (e.g., --.

<u>Column 15,</u>  
Line 51, change "2A-2E" to -- 2A-2G --.

<u>Column 16,</u>  
Lines 26, 57 and 63, change "2A-2E" to -- 2A-2G --.

<u>Column 17,</u>  
Line 1, change "an d" to -- and --.  
Line 46, change "2A-2E" to -- 2A-2G --.

Column 21, add -- * -- in blank position 30 of amino acid.  
Column 33, add -- * -- in blank position 74 of amino acid.  
Column 35, add -- * -- in blank position 22 of amino acid.

Signed and Sealed this

Seventh Day of December, 2004

JON W. DUDAS  
*Director of the United States Patent and Trademark Office*